US012644130B2

(12) United States Patent
Nissim et al.

(10) Patent No.: US 12,644,130 B2
(45) Date of Patent: Jun. 2, 2026

(54) SYSTEMS AND USES THEREOF FOR CREATING SYNTHETIC TRANSCRIPTIONAL LOGIC 'AND' GATES BASED ON PRE-mRNA TRANS-SPLICING

(71) Applicants: Migal Galilee Research Institute Ltd., Kiryat Shmona (IL); Yissum Research Development Company of The Hebrew University of Jerusalem Ltd., Jerusalem (IL)

(72) Inventors: Lior Nissim, Mevaseret Zion (IL); Gideon Gross, Moshav Almagor (IL); Hadas Weinstein-Marom, Upper Galilee (IL); Keren Roas, Jerusalem (IL)

(73) Assignees: Migal Galilee Research Institute Ltd., Kiryat Shmona (IL); Yissum Research Development Company of The Hebrew University of Jerusalem Ltd., Jerusalem (IL)

( * ) Notice: Subject to any disclaimer, the term of this patent is extended or adjusted under 35 U.S.C. 154(b) by 1199 days.

(21) Appl. No.: 17/621,067

(22) PCT Filed: Jun. 25, 2020

(86) PCT No.: PCT/IL2020/050713
§ 371 (c)(1),
(2) Date: Dec. 20, 2021

(87) PCT Pub. No.: WO2020/261277

PCT Pub. Date: Dec. 30, 2020

(65) Prior Publication Data

US 2022/0348953 A1 Nov. 3, 2022

Related U.S. Application Data

(60) Provisional application No. 62/866,229, filed on Jun. 25, 2019.

(51) Int. Cl.
*C07H 21/04* (2006.01)
*C12N 15/85* (2006.01)

(52) U.S. Cl.
CPC ........ *C12N 15/85* (2013.01); *C12N 2830/008* (2013.01); *C12N 2840/445* (2013.01)

(58) Field of Classification Search
CPC ..................... C12N 2320/33; C12N 2840/445
See application file for complete search history.

(56) References Cited

U.S. PATENT DOCUMENTS

2006/0172381 A1    8/2006    McGarrity

FOREIGN PATENT DOCUMENTS

| WO | 2009007980 A1 | 1/2009 |
| WO | 2014170480 A1 | 10/2014 |
| WO | 2016004370 A1 | 1/2016 |

OTHER PUBLICATIONS

Pergolizzi et al. (Molecular Therapy, vol. 8, No. 6, 2003, 999-1008).*
Dong, Z. et al; Transcriptional targeting of tumor endothelial cells for gene therapy. Adv. Drug Deliv. Rev. 61: pp. 542-553. (2009).
Fellig, Y et al; "H19 expression in hepatic metastases from a range of human carcinomas". J. Clin. Pathol. 58: pp. 1064-1068. (2005).
Izsvák, Z. et al; "Sleeping Beauty Transposition": Biology and Applications for Molecular Therapy. Mol. Ther. 9: pp. 147-156. (2004).
Matuskova, M et al; "Retroviral Vectors in Gene Therapy". In Advances in Molecular Retrovirology InTech. (2015).
Morel M. et al; "Cellular heterogeneity mediates inherent sensitivity-specificity tradeoff in cancer targeting by synthetic circuits" PNAS 113 (29) pp. 8133-8138. (2016).
Morgan, D. O. Cyclin-dependent kinases: engines, clocks, and microprocessors. Annu. Rev. Cell Dev. Biol. 13: pp. 261-291. (1997).
Müller, H et al. "E2Fs regulate the expression of genes involved in differentiation, development, proliferation, and apoptosis". Genes Dev. 15: pp. 267-285. (2001).
Nissim L. et al; "A tunable dual-promoter integrator for targeting of cancer cells" Molecular systems biology.(2010).
Nissim, L. et al;. "Synthetic RNA-Based Immunomodulatory Gene Circuits for Cancer Immunotherapy". Cell 171: pp. 1138-1150.e15. (2017).
Ohana, P et al; "Use of H19 regulatory sequences for targeted gene therapy in cancer". Int. J. Cancer 98: pp. 645-650 (2002).
Pergolizzi et al; "In vivo trans-splicing of 5' and 3' segments of pre-mRNA directed by corresponding DNA sequences delivered by gene transfer" Mol Ther 8(6):pp. 999-1008. (2003).

(Continued)

*Primary Examiner* — Amy Rose Hudson
(74) *Attorney, Agent, or Firm* — The Roy Gross Law Firm, LLC; Roy Gross

(57) ABSTRACT

A synthetic nucleic acid expression system for production of a transcript of interest in a predefined cell-state is provided, the system comprising (a) a first nucleic acid sequence comprising a first promoter operably linked to a nucleic acid sequence encoding a first trans-spliceable pre-mRNA sequence comprising at least one exon encoding a 5' fragment of said transcript of interest and a first RNA sequence required for spliceosome-dependent trans-splicing; and (b) a second nucleic acid sequence comprising a second promoter operably linked to a nucleic acid sequence encoding a second trans-spliceable pre-mRNA sequence comprising at least one exon encoding a 3' fragment of said transcript of interest and a second RNA sequence required for spliceosome-dependent trans-splicing; wherein said first promoter and said second promoter are different and each one is specifically regulated by said predefined cell-state.

20 Claims, 5 Drawing Sheets

Specification includes a Sequence Listing.

(56)     References Cited

OTHER PUBLICATIONS

Pergolizzi et al; "Genetic medicine at the RNA level: Modifications of the genetic repertoire for therapeutic purposes by pre-mRNA trans-splicing" Comptes Rendus Biologies 327(8):pp. 695-709. (2004).

Pleshkan, V. V et al; . "Promoters with cancer cell-specific activity for melanoma gene therapy". Acta Naturae 3: pp. 13-21. (2011).

Poddar, S. et al;. "RNA Structure Design Improves Activity and Specificity of trans-Splicing-Triggered Cell Death in a Suicide Gene Therapy Approach". Mol. Ther.—Nucleic Acids 11: pp. 41-56. (2018).

Puttaraju, M. et al;. "Spliceosome-mediated RNA trans-splicing as a tool for gene therapy." Nat. Biotechnol. 17: pp. 246-252.(1999).

Puttaraju, M et al:. "Messenger RNA repair and restoration of protein function by spliceosome-mediated RNA trans-splicing". Mol. Ther. 4: pp. 105-114. (2001).

Robson, T et al; . "Transcriptional Targeting in Cancer Gene Therapy". J. Biomed. Biotechnol. pp. 110-137. (2003).

Rushton "What Have we Learned About Synthetic Promoter Construction?" Methods Mol. Biol. 1482. (2016).

Schlesinger, J et al; "In-cell generation of antibody single-chain Fv transcripts by targeted RNA trans-splicing". J Immunol Methods 282: pp. 175-186. (2003).

Sughayer A M et al;. "The imprinted H19 gene is a marker of early recurrence in human bladder carcinoma". Mol. Pathol. 53: pp. 320-323. (2000).

Suñé-Pou, M. et al: "Targeting Splicing in the Treatment of Human Disease". Genes (Basel). 8: 87.(2017).

Tsantoulis, P. K., et al: "Involvement of E2F transcription factor family in cancer". Eur. J. Cancer 41: pp. 2403-2414. (2005).

Whitfield, M. L. et al;. "Identification of Genes Periodically Expressed in the Human Cell Cycle and Their Expression in Tumors". Mol. Biol. Cell 13: pp. 1977-2000.(2002).

Yang, Y. et al; "Spliceosome-Mediated RNA Trans-splicing". Mol. Ther. 12: pp. 1006-1012. (2005).

* cited by examiner

Final RNA

Intron

Exon 1                                                    Polypyrimidine          Exon 2
                                                              tract

5'        AGGURAGU ━━━━━━━━━━ YUNAYYYYYYYYYYYYYYYAGG                3'

5' splice junction                          Branch            3' splice junction
(Donor site)                                 point            (Acceptor site)

Module TS1
4454 bp phage f1 origin of replication

Strong acceptor site miR1 S-strand miR1 version Mv3 Intron mK-Ex1 KOZAK

Linker

SEQUENCE LISTING

```
<160> NUMBER OF SEQ ID NOS: 20

<210> SEQ ID NO 1
<211> LENGTH: 50
<212> TYPE: DNA
<213> ORGANISM: Artificial Sequence
<220> FEATURE:
<223> OTHER INFORMATION: synthetic sequence

<400> SEQUENCE: 1
tggagagatt tggatttttt ttaaaagaag agatttggag aaaggatcaa          50

<210> SEQ ID NO 2
<211> LENGTH: 50
<212> TYPE: DNA
<213> ORGANISM: Artificial Sequence
<220> FEATURE:
<223> OTHER INFORMATION: synthetic sequence

<400> SEQUENCE: 2
ttgatccttt ctccaaatct cttcttttaa attaaatcca aatctctcca          50

<210> SEQ ID NO 3
<211> LENGTH: 50
<212> TYPE: DNA
<213> ORGANISM: Artificial Sequence
<220> FEATURE:
<223> OTHER INFORMATION: synthetic sequence

<400> SEQUENCE: 3
ttgatccttt ctccaaatct cttcttttaa aaaaaatcca aatctctcca          50

<210> SEQ ID NO 4
<211> LENGTH: 30
<212> TYPE: DNA
<213> ORGANISM: Artificial Sequence
<220> FEATURE:
<223> OTHER INFORMATION: synthetic sequence
```

-continued

<400> SEQUENCE: 4
ttaaaagaag agatttggag aaaggatcaa                                    30

<210> SEQ ID NO 5
<211> LENGTH: 30
<212> TYPE: DNA
<213> ORGANISM: Artificial Sequence
<220> FEATURE:
<223> OTHER INFORMATION: synthetic sequence

<400> SEQUENCE: 5
ttgatccttt ctccaaatct cttctttaa                                     30

<210> SEQ ID NO 6
<211> LENGTH: 30
<212> TYPE: DNA
<213> ORGANISM: Artificial Sequence
<220> FEATURE:
<223> OTHER INFORMATION: synthetic sequence

<400> SEQUENCE: 6
tggagagatt tggattttt ttaaaagaag                                     30

<210> SEQ ID NO 7
<211> LENGTH: 30
<212> TYPE: DNA
<213> ORGANISM: Artificial Sequence
<220> FEATURE:
<223> OTHER INFORMATION: synthetic sequence

<400> SEQUENCE: 7 cttctttaa aaaaaatcca aatctctcca                                     30

<210> SEQ ID NO 8
<211> LENGTH: 105
<212> TYPE: DNA
<213> ORGANISM: Artificial Sequence
<220> FEATURE:
<223> OTHER INFORMATION: synthetic sequence

<400> SEQUENCE: 8
tggagagatt tggattttt ttaaaagaag agatttggag aaaggatcaa tcgcatggag     60
agatttggat ttttttaaa agaagagatt tggagaaagg atcaa                    105

<210> SEQ ID NO 9
<211> LENGTH: 50
<212> TYPE: DNA
<213> ORGANISM: Artificial Sequence
<220> FEATURE:
<223> OTHER INFORMATION: synthetic sequence

<400> SEQUENCE: 9
caagaaggta ctggctgcta ttatacgaag tgccgttgca ggatctcctg               50

<210> SEQ ID NO 10
<211> LENGTH: 50
<212> TYPE: DNA
<213> ORGANISM: Artificial Sequence
<220> FEATURE:
<223> OTHER INFORMATION: synthetic sequence

<400> SEQUENCE: 10
caggagatcc tgcaacggca cttcgtataa tagcagccag taccttcttg               50

```
<210> SEQ ID NO 11
<211> LENGTH: 50
<212> TYPE: DNA
<213> ORGANISM: Artificial Sequence
<220> FEATURE:
<223> OTHER INFORMATION: synthetic sequence

<400> SEQUENCE: 11
cattatatca tgaaacatca cttcttataa tagcattcag taccttcttg                50

<210> SEQ ID NO 12
<211> LENGTH: 50
<212> TYPE: DNA
<213> ORGANISM: Artificial Sequence
<220> FEATURE:
<223> OTHER INFORMATION: synthetic sequence

<400> SEQUENCE: 12
caagaaggta ctgaatgcta ttataagaag tgatgtttca tgatataatg                50

<210> SEQ ID NO 13
<211> LENGTH: 30
<212> TYPE: DNA
<213> ORGANISM: Artificial Sequence
<220> FEATURE:
<223> OTHER INFORMATION: synthetic sequence

<400> SEQUENCE: 13
atcaggatga tctggacgaa gagcatcagg                                      30

<210> SEQ ID NO 14
<211> LENGTH: 30
<212> TYPE: DNA
<213> ORGANISM: Artificial Sequence
<220> FEATURE:
<223> OTHER INFORMATION: synthetic sequence

<400> SEQUENCE: 14
cctgatgctc ttcgtccaga tcatcctgat                                      30

<210> SEQ ID NO 15
<211> LENGTH: 30
<212> TYPE: DNA
<213> ORGANISM: Artificial Sequence
<220> FEATURE:
<223> OTHER INFORMATION: synthetic sequence

<400> SEQUENCE: 15
tatatgaaca ttctaccaca aatcgaaaca                                      30

<210> SEQ ID NO 16
<211> LENGTH: 30
<212> TYPE: DNA
<213> ORGANISM: Artificial Sequence
<220> FEATURE:
<223> OTHER INFORMATION: synthetic sequence

<400> SEQUENCE: 16
tgtttcgatt tgtggtagaa tgttcatata                                      30

<210> SEQ ID NO 17
<211> LENGTH: 33
<212> TYPE: DNA
<213> ORGANISM: Artificial Sequence
<220> FEATURE:
<223> OTHER INFORMATION: synthetic sequence
```

-continued

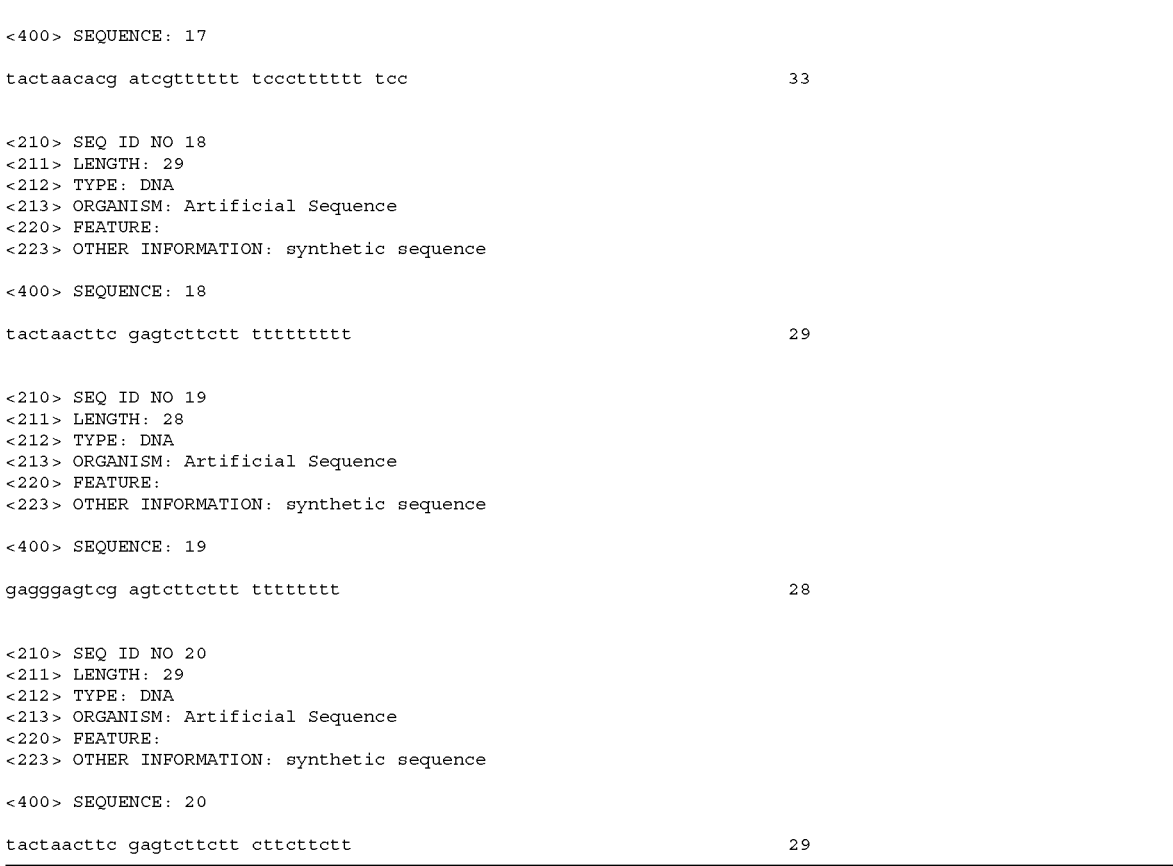

```
<400> SEQUENCE: 17
tactaacacg atcgtttttt tccctttttt tcc                                          33

<210> SEQ ID NO 18
<211> LENGTH: 29
<212> TYPE: DNA
<213> ORGANISM: Artificial Sequence
<220> FEATURE:
<223> OTHER INFORMATION: synthetic sequence

<400> SEQUENCE: 18
tactaacttc gagtcttctt ttttttttt                                               29

<210> SEQ ID NO 19
<211> LENGTH: 28
<212> TYPE: DNA
<213> ORGANISM: Artificial Sequence
<220> FEATURE:
<223> OTHER INFORMATION: synthetic sequence

<400> SEQUENCE: 19
gagggagtcg agtcttcttt ttttttt                                                 28

<210> SEQ ID NO 20
<211> LENGTH: 29
<212> TYPE: DNA
<213> ORGANISM: Artificial Sequence
<220> FEATURE:
<223> OTHER INFORMATION: synthetic sequence

<400> SEQUENCE: 20
tactaacttc gagtcttctt cttcttctt                                               29
```

SYSTEMS AND USES THEREOF FOR CREATING SYNTHETIC TRANSCRIPTIONAL LOGIC 'AND' GATES BASED ON PRE-mRNA TRANS-SPLICING

FIELD OF THE INVENTION

The present invention relates in general to expression of transcripts of interest in eukaryotic cells. In particular, the present invention provides systems for expressing transcripts regulated by an mRNA trans-splicing-based Boolean AND logic gate, i.e. expression of said transcripts occur only in the simultaneous presence of two different input signals.

BACKGROUND OF THE INVENTION

A logic gate is any type of apparatus which can perform a logical operation on one or more binary or analog inputs to produce a single binary output. A logic AND gate would only produce an output in the presence of ALL its designated inputs. In medicine, meticulous implementation of logic AND gates can enhance selectivity, safety and efficacy of current strategies attempting to express therapeutic or reporter genes in predetermined cellular conditions. For example, in vector-mediated in-vivo gene delivery, potential inputs include distinct molecular structures at the surface of the target tissue or its vasculature, specific environmental conditions (e.g. pH, oxygen concentration, presence of cytokines, chemokines, proteolytic enzymes or metabolites), the pattern of actively expressed genes and the state of their promoters or any combination of such cues. A particularly intriguing tool for implementing gene-based logic gates is 'transcriptional targeting', which, as defined in (1), " . . . involves the use of approaches in which expression of a therapeutic gene in a specific cell population is regulated by placing the gene downstream of a target cell-state specific promoter".

In a recent study, Nissim et al. (2) have demonstrated the potential of transcriptional targeting by devising two synthetic promoters for creating RNA-based gene circuits operating as logic AND gates. By carefully selecting the two promoters, P1 and P2, the authors then employed this system to confine the expression of a four-component immunomodulatory cassette to cancer cells as the only cells in the body in which both promoters P1 and P2 are active. In this system, the expression of a master transcription factor (TF, the output or gene of interest (GOI)) that controls the expression of the four genes is governed by the coordinated activity of two separate modules, each driven by one of the two synthetic promoters.

However, the strategy employed in this type of circuit inevitably allows considerable basal expression of the GOI when only one of the two promoters is active which, in various clinical applications, can lead to unwanted, potentially detrimental consequences.

SUMMARY OF INVENTION

In one aspect, the present invention provides a synthetic nucleic acid expression system for production of a transcript of interest in a predefined cell-state, the system comprising (a) a first nucleic acid sequence comprising a first promoter operably linked to a nucleic acid sequence encoding a first trans-spliceable pre-mRNA sequence comprising at least one exon encoding a 5' fragment of said transcript of interest and a first RNA sequence required for spliceosome-dependent trans-splicing; and (b) a second nucleic acid sequence comprising a second promoter operably linked to a nucleic acid sequence encoding a second trans-spliceable pre-mRNA sequence comprising at least one exon encoding a 3' fragment of said transcript of interest and a second RNA sequence required for spliceosome-dependent trans-splicing; wherein said first promoter and said second promoter are different and each one is specifically regulated by said predefined cell-state or by factors characterizing said predefined cell-state, wherein said first RNA sequence required for spliceosome-dependent trans-splicing comprises a target sequence, said second RNA sequence required for spliceosome-dependent trans-splicing comprises a guide sequence, and the target sequence is complementary to the guide sequence and hybridization of the target sequence to the guide sequence facilitates trans-splicing, and wherein the target and guide sequences lack sufficient base complementarity with each transcript of the innate transcriptome of said predefined cell-state thus prohibiting trans-splicing with said each transcript of the innate transcriptome of said predefined cell-state, and each one of said at least one exon encodes an incomplete transcript of interest, and a messenger RNA comprising the combined/trans-spliced at least one exon of said first and second trans-spliceable premRNA sequence encodes a complete transcript of interest.

In another aspect, the present invention provides a synthetic nucleic acid expression system for production of a transcript of interest, the system comprising, (a) a first nucleic acid sequence comprising a first promoter operably linked to a first trans-spliceable pre-mRNA sequence comprising at least one exon encoding a 5' fragment of said transcript of interest; and (b) a second nucleic acid sequence comprising a second promoter operably linked to a second trans-spliceable pre-mRNA sequence comprising at least one exon encoding a 3' fragment of said transcript of interest; wherein each one of said at least one exon encodes an incomplete transcript of interest, and the combined/transspliced at least one exon of said first and second transspliceable pre-mRNA sequence encode a complete transcript of interest.

In yet another aspect, the present invention provides a composition or kit comprising the first nucleic acid sequence (a) and/or the second nucleic acid sequence (b) of the synthetic expression system of any one of the above embodiments.

In still another aspect, the present invention provides a vector comprising the first nucleic acid sequence (a) and/or the second nucleic acid sequence (b) of the synthetic expression system of any one of the above embodiments. In other words, the composition or vector comprises (a) alone, (b) alone or both (a) and (b).

In an additional aspect, the present invention provides a eukaryotic cell comprising the synthetic expression system of any one of the above embodiments.

In yet an additional aspect, the present invention provides a method of expressing a transcript of interest in a eukaryotic cell comprising introducing to said eukaryotic cell the first nucleic acid sequence (a) and the second nucleic acid sequence (b) of the synthetic expression system of any one of the above embodiments, or introducing to said eukaryotic cell at least one vector of any one of the above embodiments.

In still an additional aspect, the present invention provides a method for treating a patient afflicted with a disease associated with or caused by a cell state, said method comprising contacting cells of said patient with at least one vector of the above embodiments to said patient, wherein each one of said first and second promoter independently is specifically regulated by said cell-state, and said transcript of interest encodes a transcript product facilitating treatment of said disease, thereby expressing said transcript of interest solely in said cell state and treating said disease.

In a further aspect, the present invention provides a method for selection of a eukaryotic cell introduced with more than one vector in vitro, said method comprising administering two different vectors of any one of the above embodiments, wherein one of said two vectors comprises the first nucleic acid sequence (a) but not the second nucleic acid sequence (b); and the other of said two vectors comprises the second nucleic acid sequence (b) but not the first nucleic acid sequence (a), and said transcript of interest encodes a transcript product that is essential for cell survival or a detectable gene-product.

NT, samples 23-24. Values are mean weighted median mKAte2 (CPS)±s.d from three replicate experiments. CPS, counts per second, NT, non-treated.

DETAILED DESCRIPTION OF THE INVENTION

Unlike electronic circuits, in biological systems binary inputs which can produce binary outputs are difficult to generate, as demonstrated by Nissim et al. (supra): the default state of module 1 is in fact not '0', as desired, but rather an attenuated '1'. The challenge is to optimize the safety of this strategy so that the default state of module 1 is indeed 0.

The present invention addresses this challenge by exploiting the phenomenon of mRNA trans-splicing (TS), namely, the bimolecular joining of exons from different mRNA species, which is well documented in numerous organisms and is currently explored for replacement of defective exons for treatment of inherited or acquired genetic disorders (3). TS can be targeted to pre-selected transcripts (referred to as 'targeted TS') by promoting base pairing between corresponding introns flanking the exons to be trans-spliced (see, for example, (4-6) and our own previous work (7)).

Another challenge addressed by the present invention is the selection of eukaryotic cells that have been introduced with two different DNA expression vectors, which suffers from challenges such as instability of antibiotics commonly used to select for double-transfected cells.

Figure 1:
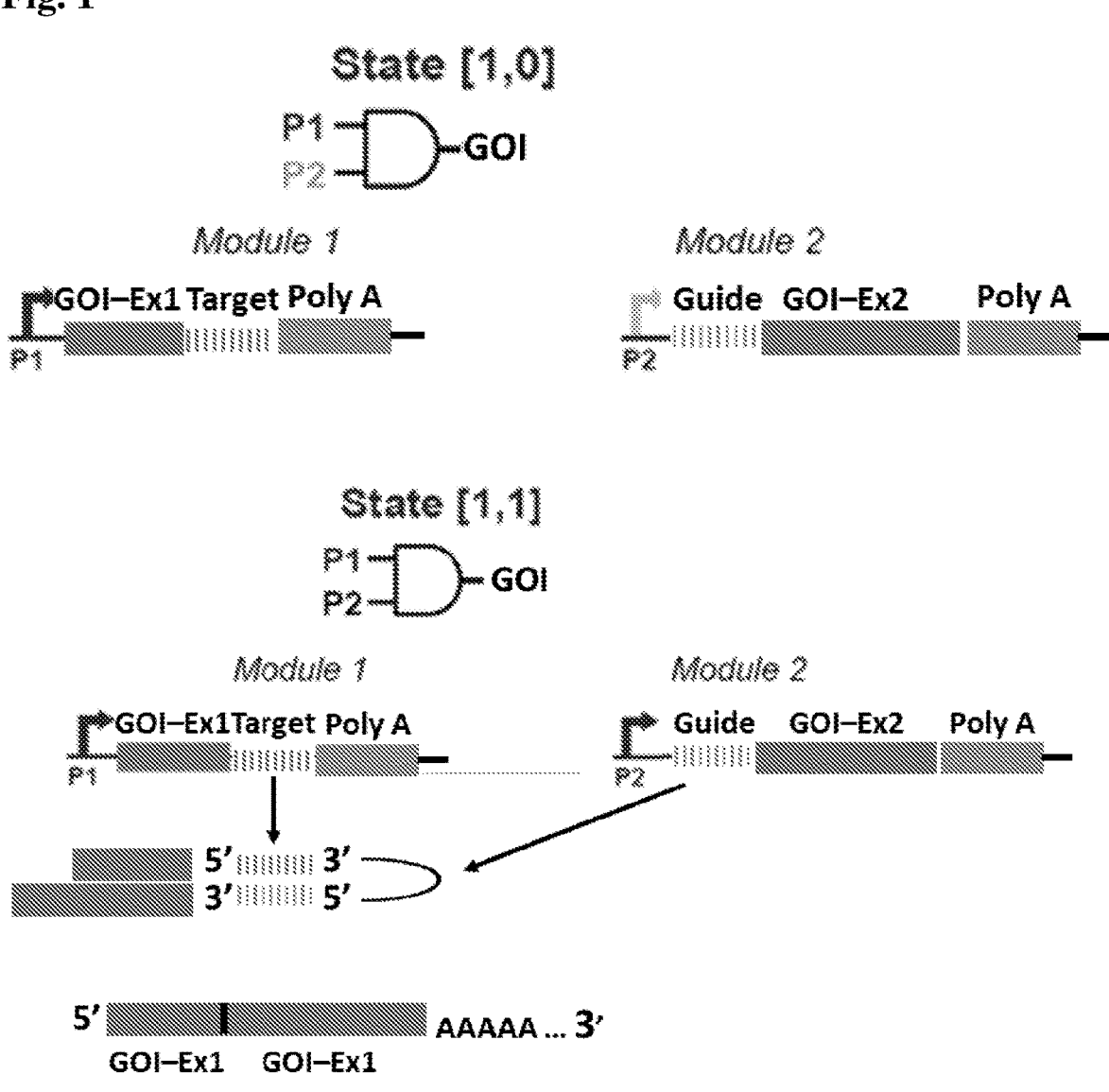
FIG. 1 shows a scheme of the proposed trans-splicing-governed circuit, based on (2). GOI, gene of interest; Ex. Exon.

Similarly to Nissim et al., the present invention provides a two-module system (FIG. 1): Module 1, driven by promoter P1, encodes the 5' end of the TF (or any GOI), including the translation initiation codon, referred to as exon 1, followed by the TS 'target' intron. Critically, NO mature, potentially hazardous protein can be translated from this module, ensuring the desired '0' state. Module 2, regulated by promoter P2, encompasses the TS 'guide' intron, followed by exon 2, which encodes the rest of the protein. Similarly, module 2 cannot produce any functional protein and, standing alone, is permanently also in state '0'. Module 2 can possess tandem repeats of the TS guide sequences so as to increase the prospects for productive TS events. Using this design, the system becomes fully dependent on the concurrent function of both promoters P1 and P2: the risk for translation of the intact TF or the polypeptide product of any GOI in cells in which promoter P1 only or promoter P2 only is active is utterly obviated.

Figure 2:
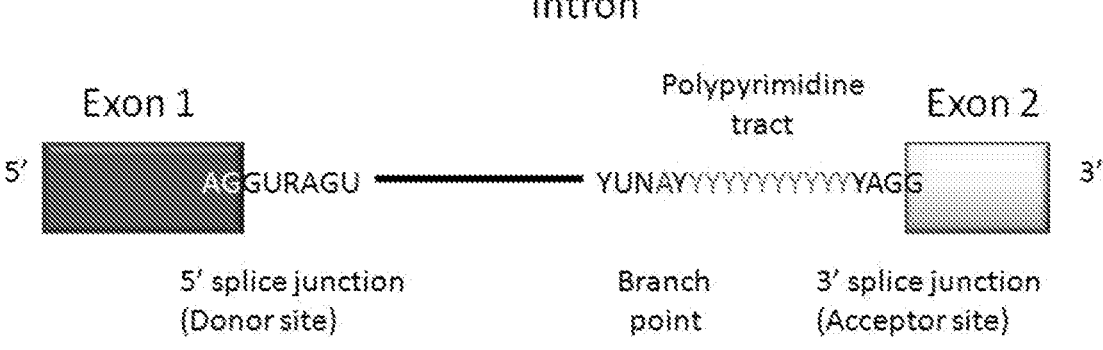
FIG. 2 depicts a schematic presentation of a typical intron (taken from https://biologydictionary.net/intron/).
Figure 3A:
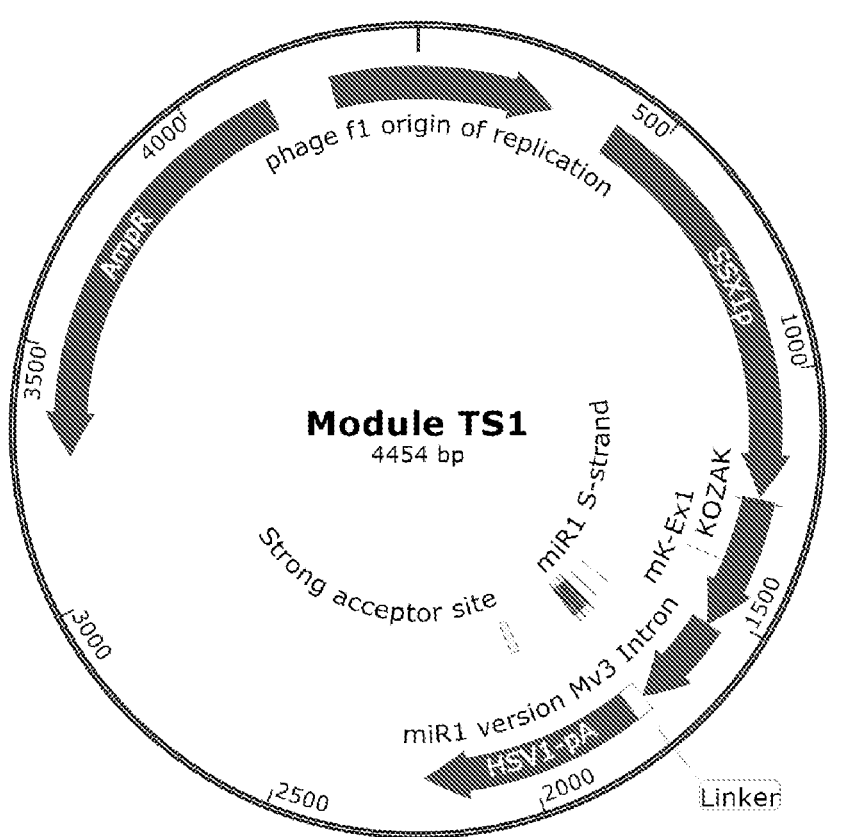
FIGS. 3A-D show maps of the four modules used in the Examples as drawn with the SnapGene software. (A) TS1. SSX1P, SSX1P promoter (2); KOZAK, optimized translation initiation codon and surrounding nucleotides; mK-Ex1, exon 1 of mKate2 gene; miR1 version Mv3 intron, an artificial intron employed by Nissim et al. (2) including the 5' basal stem to serve as the TS guiding sequence to module TS2. This sequence is followed by the 34 bp linker of the first module in (2) and the HSV1-pA, i.e. the herpes simplex virus (HSV)1 poly A site. (B) TS2. This module is designed to facilitate optimal targeted TS with the transcript of module TS1 to generate the intact mKate2 coding sequence. H2A1p, H2A1p promoter (2); miR1 AS-strand, 219 bp of the miR1 intron including the 3' basal stem as the TS1TS binding domain (BD) and the full acceptor splice site; mK-Ex2, mKate2 exon 2. (C) TS11. AFP, alpha-fetoprotein; BD, Binding Domain. (D) TS12. This module is designed to facilitate optimal targeted TS with the transcript of module TS11 to generate the intact mKate2 coding sequence. BP, branch point; Acc SS, acceptor splice site.
Figure 3B:
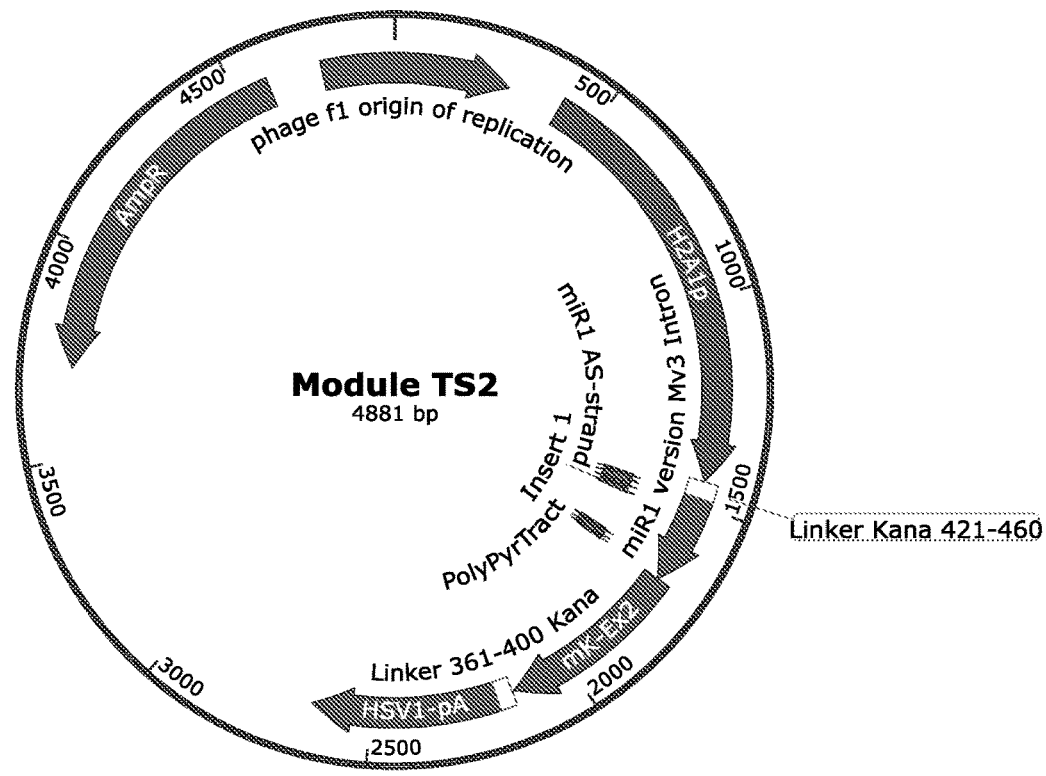
Figure 3C:
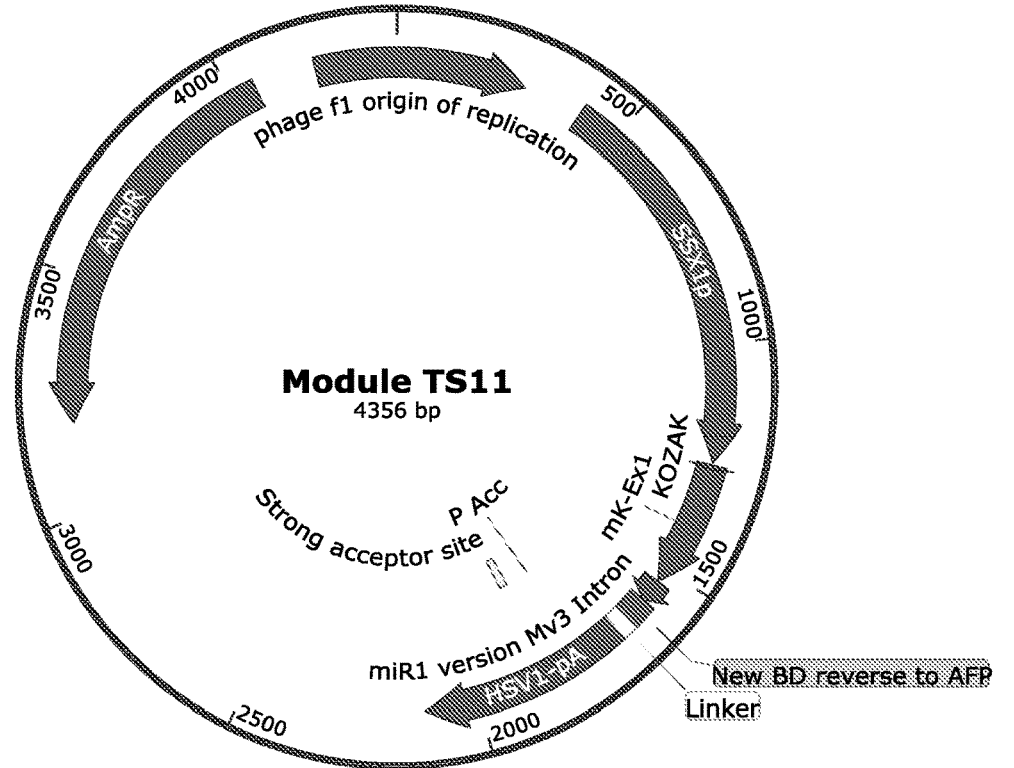
Figure 3D:
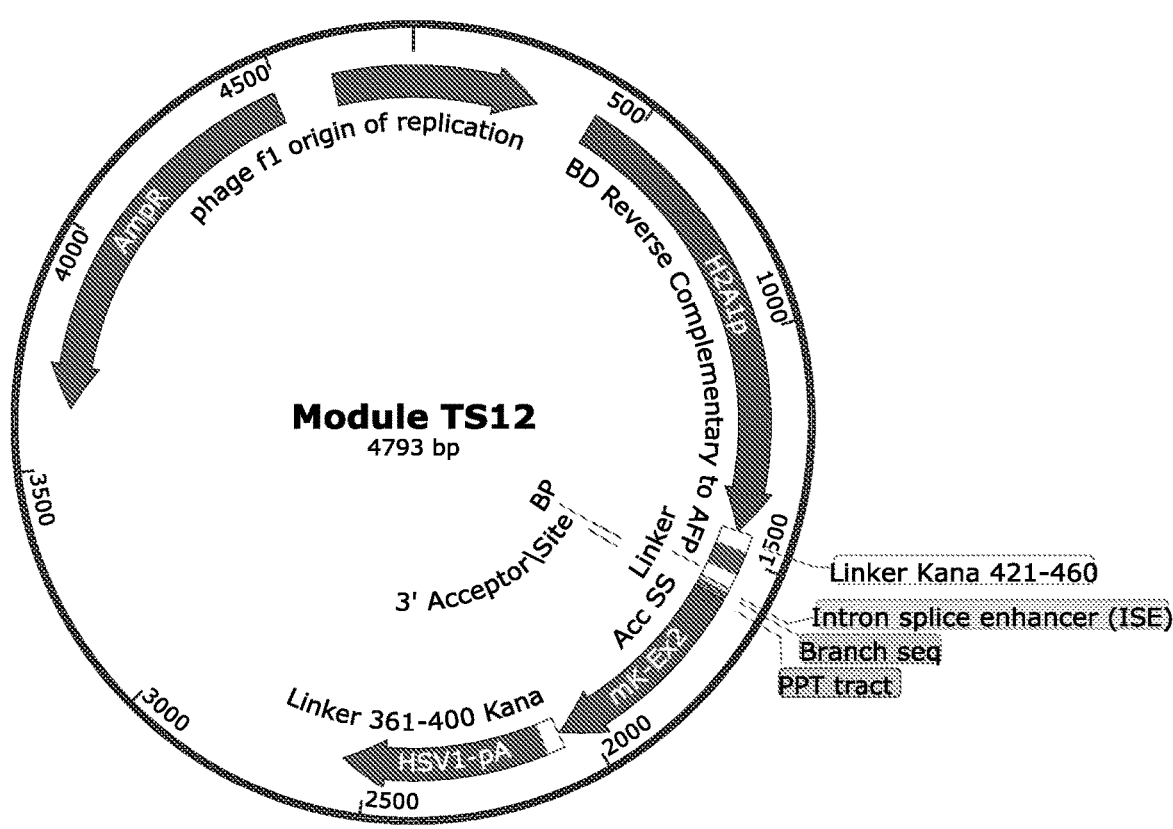

A major technological challenge facing the 'conventional' use of trans-splicing, when the target sequence in the target cell is the transcript of the endogenous gene to be corrected, is how to successfully compete with cis-splicing (8). When applying trans-splicing as proposed here, with the target transcript encoded by an exogenous gene, cis-splicing can be entirely avoided. This can be achieved by depriving the target gene of the three basic intronic elements that are mandatory for completing an efficient splicing process: the acceptor splice site, the poly-pyrimidine tract and the branch point (see FIG. 2).

The synthetic nucleic acid expression system of the present invention is a platform that enables controlled expression of a transcript of interest by splitting its sequence into two or more incomplete parts separated into different pre-mRNA sequences. Thus, as explained above regarding a dual-module system, by having each pre-mRNA sequence under the control of a separate promoter, one can ensure expression of the two pre-mRNA sequences only in the simultaneous presence of the two or more different inputs of the two or more promoters; and trans-splicing then joins these two or more sequences into on desired transcript.

This concept can be utilized for specific expression of the transcript of interest only in cells in which both inputs are present, e.g. for expression of proteins in cancer cells in a cancer patient that specifically cause cancer cell death, or for selection for specific subpopulation in a culture, such as stem cells or specific immune cells in a population isolated from bone marrow.

Indeed, it has been found in accordance with the present invention that logic AND-gate controlled trans-splicing can be utilized for completely specific expression of the transcript of interest (in this case the fluorescent protein mKate2 used in (2)) only in cells in which both inputs are present. It was further found that the precise nature of the intronic sequences used to induce TS is immaterial, since each one of the many circuits successfully tested herein completely differ; In the two modules of the first circuit tested, designated TS1 and TS2, these intronic sequences are based on the original intron separating the two mKate2 exons and represent a 'basic' TS design. Unlike, the intronic sequences in the two modules comprising the second circuit tested, TS11 and TS12, are based on a thorough analysis performed by the group of Volker et al., in a study which aimed at maximizing the efficacy of targeted TS for cancer therapy (8). Furthermore, it has been shown herein that using conventional techniques, the system can be tuned to be highly efficient by slight variations in the binding and splicing domains. This demonstrates that the synthetic nucleic acid expression system of the present invention is universal. When the optimal composition of the TS guiding and splicing elements in both modules is determined, it is suitable to serve in all possible circuits, regardless of the actual therapeutic GOI, identity of promoters or target cells chosen for a given clinical application.

In view of the above, in one aspect, the present invention provides a synthetic nucleic acid expression system for production of a transcript of interest in a predefined cell-state, the system comprising (a) a first nucleic acid sequence comprising a first promoter operably linked to a nucleic acid sequence encoding a first trans-spliceable pre-mRNA sequence comprising at least one exon encoding a 5' fragment of said transcript of interest and a first RNA sequence required for spliceosome-dependent trans-splicing; and (b) a second nucleic acid sequence comprising a second promoter operably linked to a nucleic acid sequence encoding a second trans-spliceable pre-mRNA sequence comprising at least one exon encoding a 3' fragment of said transcript of interest and a second RNA sequence required for spliceosome-dependent trans-splicing; wherein said first promoter and said second promoter are different and each one is specifically regulated by said predefined cell-state or by factors characterizing said predefined cell-state, wherein said first RNA sequence required for spliceosome-dependent trans-splicing comprises a target sequence, said second RNA sequence required for spliceosome-dependent trans-splicing comprises a guide sequence, and the target sequence is complementary to the guide sequence and hybridization of the target sequence to the guide sequence facilitates trans-splicing, and wherein the target and guide sequences lack sufficient base complementarity with each transcript of the innate transcriptome of said predefined cell-state thus prohibiting trans-splicing with said each transcript of the innate transcriptome of said predefined cell-state, and each one of said at least one exon encodes an incomplete transcript of interest, and a messenger RNA comprising the combined/trans-spliced at least one exon of said first and second trans-spliceable pre-mRNA sequence encodes a complete transcript of interest.

In certain embodiments, each one of said at least one exon does not encode, or is incapable of producing, the transcript of interest.

In certain embodiments, the first nucleic acid sequence and the second nucleic acid sequence are present on the same nucleic acid molecule.

In certain embodiments, the first and second nucleic acid sequences are present on separate nucleic acid molecules.

In certain embodiments, the synthetic nucleic acid expression system of any one of the above embodiments comprises three, four, five, or six nucleic acid sequences or more, each one comprising a promoter and a trans-spliceable pre-mRNA sequence comprising at least one exon, each exon of which encodes a different incomplete transcript of the transcript of interest. The combined/trans-spliced at least one exon of said three, four, five, six nucleic acid sequences or more trans-spliceable pre-mRNA sequences encode a complete transcript of interest.

Alternatively, the two trans-spliceable pre-mRNA sequences could bind each other due to attraction of secondary or tertiary structures on each trans-spliceable pre-mRNA sequences.

In certain embodiments, the synthetic expression system of any one of the above embodiments is characterized by at least one of the following: (i) the first RNA sequence required for spliceosome-dependent trans-splicing is located at or near the 3' end of the first nucleic acid sequence and comprises a donor site for splicing, but lacks an acceptor site for splicing, and the second RNA sequence required for spliceosome-dependent trans-splicing is located at or near the 5' end of the second nucleic acid and comprises an acceptor site for splicing, but lacks a donor site for splicing; (ii) each one of said guide sequence and said target sequence comprises a binding site sequence, which is between about 10 to about 500 nucleotides long or more; (iii) the first and the second RNA sequence required for spliceosome-dependent trans-splicing interact structurally via hybridization of the guide sequence and said target sequence—and not functionally, such as by ribozymal function; (iv) each one of said first and said second trans-spliceable pre-mRNA sequence comprises unstructured nucleotides having no internal binding and/or self-complementary sequences and therefore lacks sequences required for correct folding for forming a functional ribozyme; or (v) each one of said guide sequence and said target sequence comprises a binding site sequence, and the binding site of said guide sequence has at least one, or a plurality of, mismatch nucleotide(s) with respect to the binding site of said target sequence, or the synthetic expression system is characterized by a combination of two or more of (i) to (v).

The synthetic nucleic acid expression system of any one of the above embodiments can serve as an engineered genetic circuit providing a Boolean AND gate, in the sense that both the first and the second trans-spliceable pre-mRNA sequence is transcribed only in the simultaneous presence of the two different inputs of each one of the first and second promoter.

In certain embodiments, the 3' end of the first nucleic acid sequence of any one of the above embodiments comprises a donor site for splicing, but lacks an acceptor site for splicing; and the 5' end of the second nucleic acid comprises an acceptor site for splicing, but lacks a donor site for splicing, provided that a branch point and/or a poly-pyrimidine tract is present on at least one of the first or second nucleic acid sequence. As pointed out above, if several introns are present in the first or second trans-spliceable pre-mRNA sequence, the introns that do not facilitate trans-splicing comprise functional intronic elements that are mandatory for completing an efficient splicing process.

The binding domain of the first or second nucleic acid sequence of any one of the above embodiments comprises a target or guide sequence that are completely or partially complementary to each other, and each one of which in turn comprises a binding site sequence, which is between about 10 to about 100, 10 to about 200, 10 to about 300, 10 to about 400 or 10 to about 500 nucleotides long or more, such as between 10-20, 10-30, 10-40, 10-50, 10-60, 10-60, 10-70, 10-80, 10-90, 10-100, 10-110, 10-120, 10-130, 10-140, 10-150, 10-160, 10-170, 10-180, 10-190, 10-200, 10-210, 10-220, 10-230, 10-240, 10-250, 10-260, 10-270, 10-280, 10-290, 10-300, 20-30, 20-40, 20-50, 20-60, 20-60, 20-70, 20-80, 20-90, 20-100, 20-110, 20-120, 20-130, 20-140, 20-150, 20-160, 20-170, 20-180, 20-190, 20-200, 20-210, 20-220, 20-230, 20-240, 20-250, 20-260, 20-270, 20-280, 20-290, 20-300, 30-40, 30-50, 30-60, 30-60, 30-70, 30-80, 30-90, 30-100, 30-110, 30-120, 30-130, 30-140, 30-150, 30-160, 30-170, 30-180, 30-190, 30-200, 30-210, 30-220, 30-230, 30-240, 30-250, 30-260, 30-270, 30-280, 30-290, 30-300, 40-50, 40-60, 40-60, 40-70, 40-80, 40-90, 40-100, 40-110, 40-120, 40-130, 40-140, 40-150, 40-160, 40-170, 40-180, 40-190, 40-200, 40-210, 40-220, 40-230, 40-240, 40-250, 40-260, 40-270, 40-280, 40-290, 40-300, 50-60, 50-60, 50-70, 50-80, 50-90, 50-100, 50-110, 50-120, 50-130, 50-140, 50-150, 50-160, 50-170, 50-180, 50-190, 50-200, 50-210, 50-220, 50-230, 50-240, 50-250, 50-260, 50-270, 50-280, 50-290, 50-300, 60-70, 60-80, 60-90, 60-100, 60-110, 60-120, 60-130, 60-140, 60-150, 60-160, 60-170, 60-180, 60-190, 60-200, 60-210, 60-220, 60-230, 60-240, 60-250, 60-260, 60-270, 60-280, 60-290, 60-300, 70-80, 70-90, 70-100, 70-110, 70-120, 70-130, 70-140, 70-150, 70-160, 70-170, 70-180, 70-190, 70-200, 70-210, 70-220, 70-230, 70-240, 70-250, 70-260, 70-270, 70-280, 70-290, 70-300, 80-90, 80-100, 80-110, 80-120, 80-130, 80-140, 80-150, 80-160, 80-170, 80-180, 80-190, 80-200, 80-210, 80-220, 80-230, 80-240, 80-250, 80-260, 80-270, 80-280, 80-290, 80-300, 90-100, 90-110, 90-120, 90-130, 90-140, 90-150, 90-160, 90-170, 90-180, 90-190, 90-200, 90-210, 90-220, 90-230, 90-240, 90-250, 90-260, 90-270, 90-280, 90-290, 90-300, 100-110, 100-120, 100-130, 100-140, 100-150, 100-160, 100-170, 100-180, 100-190, 100-200, 100-210, 100-220, 100-230, 100-240, 100-250, 100-260, 100-270, 100-280, 100-290, 100-300, 110-120, 110-130, 110-140, 110-150, 110-160, 110-170, 110-180, 110-190, 110-200, 110-210, 110-220, 110-230, 110-240, 110-250, 110-260, 110-270, 110-280, 110-290, 110-300, 120-130, 120-140, 120-150, 120-160, 120-170, 120-180, 120-190, 120-200, 120-210, 120-220, 120-230, 120-240, 120-250, 120-260, 120-270, 120-280, 120-290, 120-300, 130-140, 130-150, 130-160, 130-170, 130-180, 130-190, 130-200, 130-210, 130-220, 130-230, 130-240, 130-250, 130-260, 130-270, 130-280, 130-290, 130-300, 140-150, 140-160, 140-170, 140-180, 140-190, 140-200, 140-210, 140-220, 140-230, 140-240, 140-250, 140-260, 140-270, 140-280, 140-290, 140-300, 150-160, 150-170, 150-180, 150-190, 150-200, 150-210, 150-220, 150-230, 150-240, 150-250, 150-260, 150-270, 150-280, 150-290, 150-300, 160-170, 160-180, 160-190, 160-200, 160-210, 160-220, 160-230, 160-240, 160-250, 160-260, 160-270, 160-280, 160-

290, 160-300, 170-180, 170-190, 170-200, 170-210, 170-220, 170-230, 170-240, 170-250, 170-260, 170-270, 170-280, 170-290, 170-300, 180-190, 180-200, 180-210, 180-220, 180-230, 180-240, 180-250, 180-260, 180-270, 180-280, 180-290, 180-300, 190-200, 190-210, 190-220, 190-230, 190-240, 190-250, 190-260, 190-270, 190-280, 190-290, 190-300, 200-210, 200-220, 200-230, 200-240, 200-250, 200-260, 200-270, 200-280, 200-290, 200-300, 210-220, 210-230, 210-240, 210-250, 210-260, 210-270, 210-280, 210-290, 210-300, 220-230, 220-240, 220-250, 220-260, 220-270, 220-280, 220-290, 220-300, 230-210, 230-220, 230-230, 230-240, 230-250, 230-260, 230-270, 230-280, 230-290, 240-250, 240-260, 240-270, 240-280, 240-290, 240-300, 250-260, 250-270, 250-280, 250-290, 250-300, 260-270, 260-280, 260-290, 260-300, 270-280, 270-290, 270-300, 280-290, 280-300, 290-300, nucleotides long. In certain embodiments, the binding site sequence is about 20-30, 20-40, 20-50, 20-60 in length.

In certain embodiments, the binding site is about 10, 20, 30, 40, 50, 60, 70, 80, 90, 100, 110, 120, 130, 140, 150, 160, 170, 180, 190, 200, 210, 220, 230, 240, 250, 260, 270, 280, 290, or 300 nucleotides in length. In certain embodiments, the binding site is about 50 nucleotides long.

It should be emphasized that the precise length of the binding domain/site is not crucial for the working of the nucleotide sequences of the present invention and it can be easily calibrated using methods well-known in the art, e.g. as described in the Examples below. Furthermore, it is important to notice that the binding domain may be completely synthetic in the sense that the genome of the target cell or cell state does not encode for a transcript that can bind to the binding domain. Therefore, there is no risk for trans-splicing with an endogenous transcript.

In certain embodiments, and according to Poddar et al. (8), central 2 nucleotides target mismatches are implemented into the selected binding domains (BDs) of any one of the above embodiments, generating mismatched BDs (mBDs). This is to prevent formation of long nuclear double-stranded RNA, which could trigger antisense effects, including adenosine-to-inosine (A-to-I) editing by adenosine deaminases acting on RNA (ADARs).

In certain embodiments, the target sequence (of the binding domain) of any one of the above embodiments comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150 mismatches to the guide sequence.

In certain embodiments, the target sequence comprises a sequence of nucleotides that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100% complementary to the guide sequence.

In certain embodiments, the splicing site of any one of the above embodiments is designed around a consensus sequences for the 5' splice donor site and the 3' splice region, which are well known in the art (See, Moore, et al., 1993, The RNA World, Cold Spring Harbor Laboratory Press, p. 303-358; and (8)). In addition, modified consensus sequences that maintain the ability to function as 5' donor splice sites and 3' splice regions may be used in the practice of the invention. Briefly, the 5' splice site consensus sequence is AG/GURAGU (where A=adenosine, U=uracil, G=guanine, C=cytosine, R=purine and/=the splice site). The 3' splice site consists of three separate sequence elements: the branch-point or branch site, a polypyrimidine tract and the 3' consensus sequence (YAG). The branch point consensus sequence in mammals is YNYURAC (Y=pyrimidine; N=any nucleotide). The underlined A is the site of branch formation. A polypyrimidine tract is located between the branch point and the splice site acceptor and is important for different branch point utilization and 3' splice site recognition. Recently, pre-mRNA introns referred to as U12-dependent introns, many of which begin with the dinucleotide AU and end in the dinucleotide AC, have been described. U12-dependent intron sequences as well as any sequences that function as splice acceptor/donor sequences may also be used to generate the pre-mRNA trans-splicing molecules (RTMs) of the invention.

The term "pre-mRNA trans-splicing molecule" (RTM) is used interchangeably herein with the term "synthetic nucleic acid expression system" and its nucleic acid sequence components.

An intron splice enhancer, a branch point or a polypyrimidine tract may further be introduced into the RTM as required.

A spacer/linker region to separate the acceptor splice site from the target binding domain may also be included in the RTM. The spacer/linker region may be designed to include features such as (i) stop codons which would function to block translation of any unspliced RTM and/or (ii) sequences that enhance trans-splicing to the target pre-mRNA.

The choice of an appropriate 3' acceptor site is straightforward and it can be easily calibrated to provide optimal yield using methods well-known in the art, such as those exemplified in Examples 1 and 2 below. In short, a detectable protein, such as a fluorescent protein, is encoded by the two combined nucleic acid sequences of the invention and expressed in a host cell of choice. Fluorescence intensity reflects efficiency of trans-splicing and is measured e.g. in fluorescence-activated cell sorting (FACS) instrument. This method facilitates analysis of large amounts of variations in splice sites and binding domains as shown in the Examples below, in which the following non-limiting 3' acceptor sites were used: (1) alpha-fetoprotein (AFP; SEQ ID NO: 17); (2) consensus (SEQ ID NO: 18); (3) Herpes Simplex Virus (HSV-I, SEQ ID NO: 19); and (4) pHA16 (mutated consensus sequence, SEQ ID NO: 20). It was found that certain combinations of 3' acceptor site sequence and binding domain sequence/configuration can result in up to 4-fold increase in trans-splicing efficiency (Example 2).

In certain embodiments, the predefined cell state of any one of the above embodiments is selected from a predefined cell type, tissue type, cell-cycle phase, metabolic state and pathological state.

It should be noted that a large number of transcription factors are regulated during pathological and metabolic states and the present invention contemplates cells states associated with all transcriptional regulatory sequences that are capable of binding such transcription factors. Non-limiting examples of cell states associated with known disease-regulated transcriptional regulatory sequences include cancer, neurodegenerative disease, metabolic disease and inflammation. Examples of metabolic states with known disease-regulated transcriptional regulatory sequences are high or low glucose concentration or the state of proliferation and/or senescence.

A promoter is generally known as a sequence of DNA to which proteins bind that initiate transcription of a single RNA from the DNA downstream of it. The term as used herein may include sequences upstream or downstream of the classical promoter, such as an enhancer which contributes to the regulation of transcription.

In certain embodiments, each one of said first and said second promoter of any one of the above embodiments is independently is specifically induced, activated or repressed, by said predetermined cell-state.

The term "a promoter that is induced" or "inducible promoter" as used herein refers to a promoter, which following binding of a specific extrinsic signal, such as a synthetic factor, initiates transcription of an RNA molecule.

The term "a promoter that is activated" or "activatable promoter" as used herein refers to a promoter, which following binding of a specific intrinsic signal, such as an endogenous factor, initiates transcription of an RNA molecule.

The term "a promoter that is repressed" or "repressible promoter" as used herein refers to a promoter, which down-regulates the transcription of an RNA molecule in specific cell-states.

In certain embodiments, each one of said first and said second promoter is an inducible or activatable promoter.

The term "promoter operably linked to" as used herein, refers to a promoter capable of facilitating/regulating/initiating downstream gene expression.

In certain embodiments, each one of said first and said second promoter of any one of the above embodiments is a cell-type-specific promoter, a tissue-specific promoter, a disease-specific promoter, or a cell-cycle responsive promoter.

In certain embodiments, each one of said first and said second promoter is a disease-specific promoter, such as a tumor-specific promoter, e.g. a benign tumor-specific promoter or a malignant tumor-specific promoter).

In certain embodiments, a promoter of any one of the above embodiments is a native/endogenous promoter.

The appropriate promoters chosen for a particular desired outcome facilitates specific applications of the present invention, but affect neither the safe specific expression provided by the logic AND-gate nor the efficient trans-splicing provided by the binding domain and splicing sites. The choice of a promoter is straightforward since promoters regulated by a metabolic or a pathological state are well-known in the art and methods for detecting a cell state based on the activity of a particular promoter have been developed for diseases such as cancer (9-11).

Examples of tissue- or cell-specific promoters may be found e.g. at the InvivoGene website, which teaches that tissue specific promoters are active in a specific type of cells or tissues such as B cells, monocytic cells, leukocytes, macrophages, muscle, pancreatic acinar cells, endothelial cells, astrocytes, and lung. Therefore, as non-limiting examples, the following tissue specific promoters may be used in the context of the present invention: B29 promoter (B cells), CD14 promoter (Monocytic cells), CD43 promoter (Leukocytes & platelets), CD45 promoter (Haematopoietic cells), CD68 promoter (Macrophages), Desmin promoter (Muscle), Elastase-1 promoter (Pancreatic acinar cells), Endoglin promoter (Endothelial cells), Fibronectin promoter (Differentiating cells, healing tissues), Flt-1 promoter (Endothelial cells), GFAP promoter (Astrocytes), GPIIb promoter (Megakaryocytes), ICAM-2 promoter (Endothelial cells), INF-β promoter (Hematopoietic cells), Mb promoter (Muscle), NphsI promoter (Podocytes), OG-2 promoter (Osteoblasts, Odonblasts), SP-B promoter (Lung), SYN1 promoter (Neurons), WASP promoter (Hematopoietic cells).

An example of disease-specific promoters are tumor-specific promoters, such as melanoma specific promoters as taught e.g. by Pleshkan et al. (12). Specific examples include the promoters of the human tyrosinase gene, melanoma inhibitory activity (MIA) gene, and the melacortin receptor gene.

Other examples of tissue-specific promoters used in cancer gene therapy, and which can be used in the expression system of the present invention, are prostate-specific antigen (PSA; prostate), prostate-specific membrane antigen (PSMA; prostate and vascular endothelium of other tumours), probasin (prostate), human glandular kallikrein (hK2; prostate), glial fibrillary acidic protein (GFAP; Glial/glioma), myelin basic protein (MBP; Glial and ascrocytes/glioma), myelin proteolipid protein (Glial/glioma), neural specific enolase (Neuronal/SCLC), neuronal and specific synapsin 1 (Neuronal), Ncx/Hox11L.1 (Neural crest derived cells/neuroblastoma, albumin (Liver/hepatocellular carcinoma), surfactant protein B (Type II alveolar and bronchial cells/lung cancer), thyroglobulin (Thyroid/thyroid carcinomas), and ovarian-specific promoter (ovarian) (13)

Exemplary pairs of cell-cycle transcriptional regulatory sequences that may be used in the first and second nucleic acid sequences of any one of the above embodiments are found in WO 2009/007980 and in 14-17.

Each one of the above references teaching disease and tissue specific promoters is incorporated as if fully disclosed herein.

The design of efficient expression systems is well-known in the art. For example, the expression system of the present invention may include a TATA box and other upstream elements determining the rate at which transcription is initiated as well as different types of promoters, enhancers, and polyadenylation sequences, the combination of which contributes to optimal transcription (see e.g. WO 2009/007980).

In certain embodiments, a promoter of any one of the above embodiments is a synthetic promoter.

The art of designing synthetic promoters is well-known and can be used in the first and second nucleic acid sequences of the present invention e.g. according to (18), and publications cited therein. In short, promoters are modular, consisting of combinations of cis-acting elements that are the binding sites for transcription factors, and it is this promoter architecture that largely determines the expression pattern of a gene. The modular nature of promoters is supported by the observation that many cis-acting elements retain their activities when they are taken out of their native promoter context and used as building blocks in synthetic promoters. We therefore have a large collection of cis-acting elements to use in building synthetic promoters and many minimal promoters upon which to build them. Examples of additional synthetic promoters that could be used in the nucleic acid molecules of any one of the above embodiments are disclosed in US20170002378A1 incorporated by reference as if fully disclosed herein.

In certain embodiments, each one of the promoters of any one of the above embodiments is different from any other promoter comprised in the synthetic nucleic acid expression system of the present invention and is regulated by a different input signal/condition.

In certain embodiments, the first promoter of any one of the above embodiments is different from the second promoter and the first and second promoters are regulated/activated/induced by a different input signal/condition.

In certain embodiments, the second nucleic acid sequence of any one of the above embodiments comprises tandem repeats of one guide sequence.

In any case, the exon(s) on the first or second trans-spliceable pre-mRNA sequence of any one of the above embodiments encode an incomplete transcript, which is different from the transcript of interest. In certain embodiments, the incomplete transcript of interest is a non-functional transcript or encodes a non-functional protein.

In certain embodiments, the transcript of interest of any one of the above embodiments encodes a transcription factor, e.g. a synthetic transcription factor; a chemokine; a cytokine; a checkpoint inhibitor; an auxotrophic marker; an enzyme; a growth factor; a reporter gene; a short hairpin RNA (shRNA), or a micro RNA (miRNA). Each possibility represents a separate embodiment. One non-limiting example of a synthetic transcription factor is GAD, a fusion of yeast GAL4 DNA-binding domain to viral VP16 transcriptional activation domain.

In certain embodiments, the first nucleic acid sequence and said second nucleic acid sequence are present on the same nucleic acid molecule or the first and second nucleic acid sequences are present on separate nucleic acid molecules; the synthetic expression system of the present invention is characterized by at least one of the following: (i) the first RNA sequence required for spliceosome-dependent trans-splicing is located at or near the 3' end of the first nucleic acid sequence and comprises a donor site for splicing, but lacks an acceptor site for splicing, and the second RNA sequence required for spliceosome-dependent trans-splicing is located at or near the 5' end of the second nucleic acid and comprises an acceptor site for splicing, but lacks a donor site for splicing; (ii) each one of said guide sequence and said target sequence comprises a binding site sequence, which is between about 10 to about 500 nucleotides long or more; (iii) the first and the second RNA sequence required for spliceosome-dependent trans-splicing interact structurally via hybridization of the guide sequence and said target sequence—and not functionally, such as by ribozymal function; (iv) each one of said first and said second trans-spliceable pre-mRNA sequence comprises unstructured nucleotides having no internal binding and/or self-complementary sequences and therefore lacks sequences required for correct folding for forming a functional ribozyme; or (v) each one of said guide sequence and said target sequence comprises a binding site sequence, and the binding site of said guide sequence has at least one, or a plurality of, mismatch nucleotide(s) with respect to the binding site of said target sequence, or the synthetic expression system is characterized by a combination of two or more of (i) to (v); said predefined cell state is selected from a predefined cell type, tissue type, cell-cycle phase, metabolic state and pathological state; said incomplete transcript of interest is a non-functional transcript or encodes a non-functional protein; and said transcript of interest encodes a transcription factor, e.g. a synthetic transcription factor; a chemokine; a cytokine; a checkpoint inhibitor; an auxotrophic marker; an enzyme; a growth factor; a reporter gene; a short hairpin RNA (shRNA), or a micro RNA (miRNA).

In particular embodiments, each one of said first and said second promoter independently is specifically induced or activated by said predetermined cell-state; and each one of said first and said second promoter is a cell-type-specific promoter, a tissue-specific promoter, a disease-specific promoter or a cell-cycle responsive promoter.

In particular embodiments, each one of said first and said second promoter is a disease-specific promoter, such as a tumor-specific promoter.

The platform disclosed herein may be utilized for controlled expression of a transcript in vitro under specific conditions. In a non-limiting example, the present disclosure may be utilized for selection of multiple plasmids in eukaryotic cells, without requiring multiple antibiotic markers. In one non-limiting example, the present invention provides for selection of, for example, six co-transfected plasmids using only 3 antibiotic markers. The selection of multiple transfected cells may be achieved by having the separate pre-mRNA sequences encoded on separate DNA molecules. In another example, an auxotrophic cell culture grown in the absence of an element essential for its survival can be used to select for cells transfected with multiple DNA molecules encoding a gene product enabling growth that is expressed only in the presence of both DNA molecules. In both cases, the promoters controlling the transcription of the multiple separate incomplete transcripts can be identical and even constitutive.

Therefore in another aspect, the present invention provides a second synthetic nucleic acid expression system for production of a transcript of interest, the system comprising, (a) a first nucleic acid sequence comprising a first promoter operably linked to a first trans-spliceable pre-mRNA sequence comprising at least one exon encoding a 5' fragment of said transcript of interest; and (b) a second nucleic acid sequence comprising a second promoter operably linked to a second trans-spliceable pre-mRNA sequence comprising at least one exon encoding a 3' fragment of said transcript of interest; wherein each one of said at least one exon encodes an incomplete transcript of interest, and the combined/trans-spliced at least one exon of said first and second trans-spliceable pre-mRNA sequence encode a complete transcript of interest.

The above second expression systems thus enables the production of a complete transcript of interest by trans-splicing of said at least one exon encoding the 5' fragment of said transcript of interest and said at least one exon encoding the 3' fragment of said transcript of interest.

In certain embodiments, the second synthetic nucleic acid expression system comprises three, four, five, or six nucleic acid sequences or more, each one comprising a promoter and a trans-spliceable pre-mRNA sequence comprising at least one exon, each exon of which encodes a different incomplete transcript of the transcript of interest. The combined/trans-spliced at least one exon of said three, four, five, six or more trans-spliceable pre-mRNA sequences encodes a complete transcript of interest.

In certain embodiments, the trans-spliceable pre-mRNA sequences of any one of the above embodiments, further comprises a nucleic acid sequence that enables the binding of one trans-spliceable pre-mRNA sequence to another trans-spliceable pre-mRNA sequence and thus facilitates trans-splicing In particular, each one of said first and second trans-spliceable pre-mRNA sequence further comprises a nucleic acid sequence that enables the binding of said first trans-spliceable pre-mRNA sequence to said second trans-spliceable pre-mRNA sequence and thus facilitates trans-splicing.

When any one of the trans-spliceable pre-mRNA sequences comprised in any one of the synthetic nucleic acid expression systems of the present invention comprises more than one exon, the exons are interspersed with introns and it should be understood that in any configuration there will always be functional intronic elements that are mandatory for completing an efficient cis-splicing process (acceptor and donor splice sites, the poly-pyrimidine tract and the branch point) present in these introns that facilitate excision of the introns. However, it is also made clear that cis-splicing within the first or second trans-spliceable pre-mRNA sequence cannot result in an RNA comprising or encoding the complete transcript of interest. Furthermore, as explained below, the first or second trans-spliceable pre-mRNA sequence is designed to prevent cis-splicing of the intron necessary for trans-splicing.

The nucleic acid constructs of any one of the above embodiments may be prepared by any suitable method, including, for example, cloning and restriction of appropriate sequences or direct chemical synthesis by methods such as the phosphotriester method of Narang et al. (1979) Meth. Enzymol. 68: 90-99; the phosphodiester method of Brown et al. (1979) Meth. Enzymol. 68: 109-151, the diethylphosphoramidite method of Beaucage et al. (1981) Tetra. Lett., 22: 1859-1862; and the solid support method of U.S. Pat. No. 4,458,066.

In yet another aspect, the present invention provides a composition or kit comprising the first nucleic acid sequence (a) and/or the second nucleic acid sequence (b) of the synthetic expression system of any one of the above embodiments.

Matuskova and Durinikova (19) teach that there are two systems for the delivery of transgenes into a cell—viral and non-viral. The non-viral approaches are represented by polymer nanoparticles, lipids, calcium phosphate, electroporation/nucleofection or biolistic delivery of DNA-coated microparticles or mRNA. The non-viral approach also provides transposon systems, such as the transposon system commonly known as "Sleeping Beauty" (for protocols using Sleeping Beauty transposons see for example (20).

The viral approach provides two main types of vectors that can be used in accordance with the present invention depending on whether the DNA is integrated into chromatin of the host cell or not. Retroviral vectors such as those derived from gammaretroviruses or lentiviruses persist in the nucleus as integrated provirus and reproduce with cell division. Other types of vectors (e.g. those derived from herpesviruses or adenoviruses) remain in the cell in the episomal form.

In still another aspect, the present invention provides a vector comprising the first nucleic acid sequence (a) and/or the second nucleic acid sequence (b) of the synthetic expression system of any one of the above embodiments. In other words, the composition or vector comprises (a) alone, (b) alone or both (a) and (b).

In certain embodiments, the vector comprises the first nucleic acid sequence (a) or the second nucleic acid sequence (b) of the synthetic expression system of any one of the above embodiments; but not both the first nucleic acid sequence (a) and the second nucleic acid sequence (b).

In certain embodiments, the vector of any one of the above embodiments is a DNA vector, such as a plasmid or viral vector; or a non-viral vector, such as a polymer nanoparticle, lipid, calcium phosphate, DNA-coated microparticle or transposon.

In certain embodiments, the DNA vector is a viral vector selected from a modified virus derived from a virus selected from the group consisting of a retrovirus, lentivirus, gammavirus, adenovirus, adeno-associated virus, pox virus, alphavirus, and herpes virus.

In an additional aspect, the present invention provides a eukaryotic cell comprising the synthetic expression system of any one of the above embodiments.

In yet an additional aspect, the present invention provides a method of expressing a transcript of interest in a eukaryotic cell comprising introducing to said eukaryotic cell the first nucleic acid sequence (a) and the second nucleic acid sequence (b) of the synthetic expression system of any one of the above embodiments, or introducing to said eukaryotic cell at least one vector of any one of the above embodiments.

In certain embodiments, the composition comprising the first nucleic acid sequence (a) or the second nucleic acid sequence (b) of the synthetic expression system of any one of the above embodiments, or the vector of any one of the above embodiments, is a pharmaceutical composition further comprising a pharmaceutically acceptable carrier.

In certain embodiments, said introducing is performed in vitro, in vivo or ex vivo.

In still an additional aspect, the present invention provides at least one vector of any one of the above embodiments for use in treating a patient or cells obtained from said patient afflicted with a disease associated with or caused by a cell state, wherein said use comprises contacting cells of said patient with at least one of said vector, wherein each one of said first and second promoter independently is specifically regulated by said cell-state, and said transcript of interest encodes a transcript product facilitating treatment of said disease, thereby expressing said transcript of interest solely in said cell state and treating said disease.

In a similar aspect, the present invention provides a method for treating a patient afflicted with a disease associated with or caused by a cell state, said method comprising contacting cells of said patient with at least one vector of the any one of the above embodiments to said patient, wherein each one of said first and second promoter independently is specifically regulated by said cell-state, and said transcript of interest encodes a transcript product facilitating treatment of said disease, thereby expressing said transcript of interest solely in said cell state and treating said disease.

In another similar aspect, the present invention provides use of at least one vector of any one of the above embodiments in the manufacture of a medicament for the treatment of a patient or cells obtained from said patient afflicted with a disease associated with or caused by a cell state, wherein said use comprises contacting cells of said patient with at least one of said vector, wherein each one of said first and second promoter independently is specifically regulated by said cell-state, and said transcript of interest encodes a transcript product facilitating treatment of said disease, thereby expressing said transcript of interest solely in said cell state and treating said disease.

In certain embodiments, the use or method comprises contacting said cells with two different vectors, wherein one of said two vectors comprises the first nucleic acid sequence (a) but not the second nucleic acid sequence (b); and the other of said two vectors comprises the second nucleic acid sequence (b) but not the first nucleic acid sequence (a).

In certain embodiments, the contacting is performed in vitro, in vivo or ex vivo.

In case the contacting is performed in vitro or ex vivo, cells from the patients or from other subjects are obtained, contacted with said at least one vector and then returned to the patient (e.g. adoptive cell transfer therapy). Thus, the cells transduced with the at least one vector are for use in treating the disease or for use in the manufacture of a medicament for the treatment of the disease.

In case the contacting is performed in vivo, a therapeutically effective amount of said at least one vector is administered to the patient and the vectors contact the target cells in situ.

In certain embodiments, the cell state is selected from a cell type, tissue type, cell-cycle phase, metabolic state, pathological state, differentiation state, epigenetic state, and activation state.

In certain embodiments, each one of said first and said second promoter independently is specifically induced or activated by said predetermined cell-state.

In certain embodiments, each one of said first and said second promoter independently is selected from a cell-type-specific promoter, a tissue-specific promoter, a disease-specific promoter, a differentiation state specific promoter, an epigenetic state specific promoter, an activation state specific promoter and a cell-cycle responsive promoter.

In certain embodiments, the exon(s) on the first and second trans-spliceable pre-mRNA sequence encode an incomplete transcript, which is different from the transcript of interest; and the incomplete transcript of interest is a non-functional transcript or encodes a non-functional protein.

In certain embodiments, each one of said first and said second promoter is a disease-specific promoter, such as a tumor-specific promoter.

In certain embodiments, the patient is a human patient.

In certain embodiments, the disease is cancer and each one of said first and said second promoter is a tumor-specific promoter.

In certain embodiments, the transcript product facilitating treatment of said disease is a transcription factor, e.g. synthetic transcription factor; a chemokine; a cytokine; a checkpoint inhibitor; an enzyme; a growth factor; a reporter gene; a short hairpin RNA (shRNA), or a micro RNA (miRNA).

In certain embodiments, the method comprises contacting said cells with two different vectors, wherein one of said two vectors comprises the first nucleic acid sequence (a) but not the second nucleic acid sequence (b), and the other of said two vectors comprises the second nucleic acid sequence (b) but not the first nucleic acid sequence (a); said contacting is performed in vitro, in vivo or ex vivo; said cell state is selected from a cell type, tissue type, cell-cycle phase, metabolic state, pathological state, differentiation state, epigenetic state, and activation state; and said transcript product facilitating treatment of said disease is a transcription factor, e.g. synthetic transcription factor; a chemokine; a cytokine; a checkpoint inhibitor; an enzyme; a growth factor; a reporter gene; a short hairpin RNA (shRNA), or a micro RNA (miRNA).

In certain embodiments, each one of said first and said second promoter independently is specifically induced or activated by said predetermined cell-state; or each one of said first and said second promoter independently is selected from a cell-type-specific promoter, a tissue-specific promoter, a disease-specific promoter, a differentiation state specific promoter, an epigenetic state specific promoter, an activation state specific promoter or a cell-cycle responsive promoter.

In certain embodiments, each one of said first and said second promoter is a disease-specific promoter, such as a tumor-specific promoter; and said patient is a human patient.

In certain embodiments, the disease is cancer, said eukaryotic cell is a tumor cell, and each one of said first and said second promoter is a tumor-specific promoter.

In a further aspect, the present invention provides a method for selection of a eukaryotic cell introduced with more than one vector in vitro, said method comprising administering two different vectors of any one of the above embodiments, wherein one of said two vectors comprises the first nucleic acid sequence (a) but not the second nucleic acid sequence (b); and the other of said two vectors comprises the second nucleic acid sequence (b) but not the first nucleic acid sequence (a), and said transcript of interest encodes a transcript product that is essential for cell survival or a detectable gene-product.

In certain embodiments, the method for selection comprises administering more than two different vectors of any one of the above embodiments, wherein each vector carries a nucleic acid sequence encoding a different exon than any other nucleic acid sequence carried by other vectors, and each exon comprises or encodes a different incomplete transcript of interest.

In certain embodiments, each one of said first and second promoter used in the method for selection is a constitutive promoter.

In certain embodiments, each one of said first and second promoter is an inducible or activatable promoter. The inducible or activatable promoters may be identical or different and may be regulated/induced/activated by identical of different inputs.

In certain embodiments, the eukaryotic cell is an auxotroph and is grown in a growth medium lacking an element essential for the cell's survival and said gene product that is essential for cell survival is an auxotrophic marker (e.g. as taught in Wikipedia under "Commonly used auxotrophic markers").

In certain embodiments, the detectable gene-product is an enzyme, such as Luciferase, or a fluorescent protein, such as green fluorescent protein (GFP).

In certain embodiments, the eukaryotic cell is a yeast, mouse, rat, insect, fish, avian or human cell.

Definitions

The term "nucleic acid sequence" as used herein refers to the sequence per se and also to a nucleic acid molecule comprising a nucleic acid sequence. For example, a synthetic nucleic acid expression system comprising a nucleic acid sequence is equivalent to a synthetic nucleic acid expression system comprising a nucleic acid molecule comprising a nucleic acid sequence.

It is expected that during the life of a patent maturing from this application many relevant promoters/expression products/binding domains/splice sites/will be discovered and the scope of the terms "transcriptional regulatory sequence" "binding domain", "splicing site", "acceptor site", "donor site" etc. and "expression product" are intended to include all such new sequences and polypeptides.

As used herein, the terms "subject" or "individual" or "animal" or "patient" or "mammal," refers to any subject, particularly a mammalian subject, for whom diagnosis, prognosis, or therapy is desired, for example, a human.

The term "treating" as used herein refers to means of obtaining a desired physiological effect. The effect may be therapeutic in terms of partially or completely curing a disease and/or symptoms attributed to the disease. The term refers to inhibiting the disease, i.e. arresting its development; or ameliorating the disease, i.e. causing regression of the disease.

Pharmaceutical compositions for use in accordance with the present invention may be formulated in conventional manner using one or more physiologically acceptable carriers or excipients. The carrier(s) must be "acceptable" in the sense of being compatible with the other ingredients of the composition and not deleterious to the recipient thereof.

Methods of administration include, but are not limited to, parenteral, e.g., intravenous, intraperitoneal, intramuscular, subcutaneous, mucosal (e.g., oral, intranasal, buccal, vaginal, rectal, intraocular), intrathecal, topical and intradermal routes. Administration can be systemic or local. In certain embodiments, the pharmaceutical composition is adapted for oral administration.

The term "carrier" refers to a diluent, adjuvant, excipient, or vehicle with which the active agent is administered. The carriers in the pharmaceutical composition may comprise a binder, such as microcrystalline cellulose, polyvinylpyrrolidone (polyvidone or povidone), gum tragacanth, gelatin, starch, lactose or lactose monohydrate; a disintegrating agent, such as alginic acid, maize starch and the like; a lubricant or surfactant, such as magnesium stearate, or sodium lauryl sulphate; and a glidant, such as colloidal silicon dioxide.

The following exemplification of carriers, modes of administration, dosage forms, etc., are listed as known possibilities from which the carriers, modes of administration, dosage forms, etc., may be selected for use with the present invention. Those of ordinary skill in the art will understand, however, that any given formulation and mode of administration selected should first be tested to determine that it achieves the desired results.

The term "therapeutically effective amount" as used herein means an amount of the nucleic acid sequence/molecule or vector that will elicit the biological or medical response of a tissue, system, animal or human that is being sought, i.e. treatment of a disease associated with or caused by a cell state, such as cancer. The amount must be effective to achieve the desired therapeutic effect as described above, depending inter alia on the type and severity of the condition to be treated and the treatment regime. The therapeutically effective amount is typically determined in appropriately designed clinical trials (dose range studies) and the person skilled in the art will know how to properly conduct such trials to determine the effective amount. As generally known, an effective amount depends on a variety of factors including the affinity of the ligand to the receptor, its distribution profile within the body, a variety of pharmacological parameters such as half-life in the body, on undesired side effects, if any, and on factors such as age and gender, etc.

Unless otherwise indicated, all numbers used in this specification are to be understood as being modified in all instances by the term "about". Accordingly, unless indicated to the contrary, the numerical parameters set forth in this specification are approximations that may vary by up to plus or minus 10% depending upon the desired properties to be obtained by the present invention.

The invention will now be illustrated by the following non-limiting Examples.

EXAMPLES

Example 1. Specific and Efficient Expression of Gene of Interest

General considerations. Our main objective in this project was to demonstrate a proof of concept of our new TS-based circuit, namely, showing inside living cells that:

The mature protein product of the two-module circuit is only synthesized when both module 1 (driven by promoter P1) and module 2 (driven by promoter P2) are co-expressed, but is absolutely absent when each of the two modules is expressed alone.

Whereas zero background is inherent to our design, maximizing its actual yield, that is, level of the mature protein product synthesized when both modules are fully active, would require careful optimization steps (see, for example, the original Nissim paper (2) and, especially the supplementary material). While these have naturally been beyond the scope of our current iGEM endeavor, they are certainly in the focus of our future plans. One should remember that this system is UNIVERSAL. When the optimal composition of the TS guiding elements in both modules is determined, it could serve in all possible circuits, regardless of the actual therapeutic GOI, identity of promoters or target cells chosen for a given clinical application.

Experimental design. To achieve this goal we have assembled an experimental in-cell system comprising the following components:

Cells: We have chosen human HEK293T cells (293T ATCC®; CRL-3216™ *Homo sapiens* embryonic kidney), which are easy to propagate and transfect.

Gene delivery: In our preparatory experiments we have found that transient expression of plasmid DNA in HEK293T cells using improved lipid reagents, such as FuGENE HD transfection reagent (Promega), can approach 100% efficacy with practically no cell death (not shown).

Gene of interest: For demonstrating a proof of concept we have used the same mKate2 reporter gene used by Nissim et al. (see (2) and FIG. 1), which is easy to detect by flow cytometry. We have preserved the original division of the gene to two exons as in (2).

Circuits: In the current study we have assembled and analyzed two different circuits, each comprising two modules (see below for details). While sharing elements such as promoters, poly A sites, etc., the intronic sequences selected to induce TS in each of the two circuits completely differ. In the two modules of the first circuit, designated TS1 and TS2, these intronic sequences are based on the original intron separating the two mKate2 exons used in (2) and represent a 'basic' TS design. Unlike, the intronic sequences in the two modules comprising the second circuit, TS11 and TS12, are based on a thorough analysis performed by the group of Volker Patzel from the National University of Singapore, a world leader in mRNA TS, in a study which aimed at maximizing the efficacy of targeted TS for cancer therapy (8).

Vector: For expressing Module 1 in each circuit we have used the expression vector pLN193 and for Module 2 we have used pLN75. Description of the different components incorporated into these vectors, including their full DNA sequence, is available in the suppl. material of (2).

Gene Composition of the Two Circuits:

Module TS1: Expression of module TS1 is driven by the SSX1p promoter, which was used by Nissim et al. and is active in HEK293 cells (2). As argued above, our circuits are based on TS events designed to take place between the transcripts of two exogenously introduced modules, thus allowing full degree of freedom in selecting the optimal guiding sequences. Here, downstream to exon 1 of mKate2 we have introduced the first 198 bp of the miR1 intron employed by Nissim et al. (2), including the 5' basal stem to serve as the TS guiding sequence to module TS2. This sequence is followed by the 34 bp linker of the first module in (2) and the HSV1 pA poly A site.

Module TS2: This module is designed to facilitate optimal targeted TS with the transcript of module TS1 to generate the intact mKate2 coding sequence. Its expression is driven by the H2A1p promoter (2), followed by a 40 bp linker (positions 421-460 in the kanamycin resistance gene of thermophilic bacillus from plasmid pTB913 (GenBank accession K02551.1)) and the remaining 219 bp of the miR1 intron, including the 3' basal stem as the TS1 TS binding domain (BD) and the full acceptor splice site, followed by mKate2 exon 2, 40 bp linker (positions 361-400 in the kanamycin resistance gene), BamHI and HindIII restriction sites and the HSV1 pA poly A site.

Module TS11: Similarly to TS1, the promoter of this module is SSX1p. In module TS11, immediately 3' to exon 1 of mKate2 we inserted the first 50 bp of the mKate2 intron (2) in order to fully preserve the strong donor splice site and to provide a linker preceding the TS guiding sequence. Here we have chosen to adapt the optimized TS elements which have recently been reported in (8). This paper describes in full detail the design of RNA structures, which improve both activity and specificity of TS-mediated targeting of the herpes simplex virus thymidine kinase coding sequence to the endogenous alpha-fetoprotein (AFP) transcript, as suicide gene therapy of cancer. In particular, we have chosen the optimized 50 bp sequence derived from intron 5 of AFP (NCBI Reference Sequence: NG_023028.1). Yet, adapting exactly the same sequence as in (8) poses a problem as the AFP gene is expressed in HEK293 cells (as shown in FIG. S1C in (8)) and the expected TS may be dampened by binding to the endogenous transcript. In order to avoid such an undesired outcome yet preserve the favorable properties of the selected stretch, we have simply chosen to invert the 50 bp sequence from intron 5. The inverted sequence also preserves an artificial 2-base mismatch, introduced by the Patzel group "to prevent formation of long nuclear double-stranded RNA, which could trigger antisense effects" (8). The final TS guiding sequence in module 1 is (mismatch is marked bold):

(SEQ ID NO: 1)

5'TGGAGAGATTTGGATTTTTTTTTAAAAGAAGA

GATTTGGAGAAAGGATCAA 3'

This TS guiding sequence is followed by a 34 bp linker and the HSV1 pA poly A site, as in (2).

Module TS12: Expression is driven by the H2A1p promoter. The promoter sequence is followed by the 40 bp linker of the kanamycin resistance gene (positions 421-460). The TS binding domain (BD) in module TS12 is the reverse complementary of the AFP-based TS guiding sequence of module 1 with the 2 nucleotide mismatch (in bold):

(SEQ ID NO: 2)

5'TTGATCCTTTCTCCAAATCTCTTCTTTTAAATT

AAATCCAAATCTCTCCA 3'

This TS BD is followed by the 34 bp linker which precedes the HSV1 pA poly A (2) and the intron splice enhancer, branch point, polypyrimidine tract and the acceptor splice site, all taken from (8), continuing with mKate2 exon 2, 40 bp linker (positions 361-400 in the kanamycin resistance gene) and the HSV1 pA poly A site.

For plasmid maps of all four new modules see FIGS. 3A-D.

Results. To obtain a proof of concept, we have designed a co-transfection experiment in HEK293 cells. We first confirmed that the two promoters we have selected for our system, SSX1p (modules TS1 and TS11) and H2A1p (modules TS2 and TS12), are indeed active in HEK293T cells. To this end we have transiently transfected HEK293 cells with either plasmid pLN74, which encodes the intact mKate2 protein under the SSX1p promoter or plasmid pLN75 in which ECFP is driven by the H2A1p promoter (2). Indeed, transfection of either plasmid, but not irrelevant DNA, resulted in intense fluorescence of the respective protein (not shown).

Figure 4:
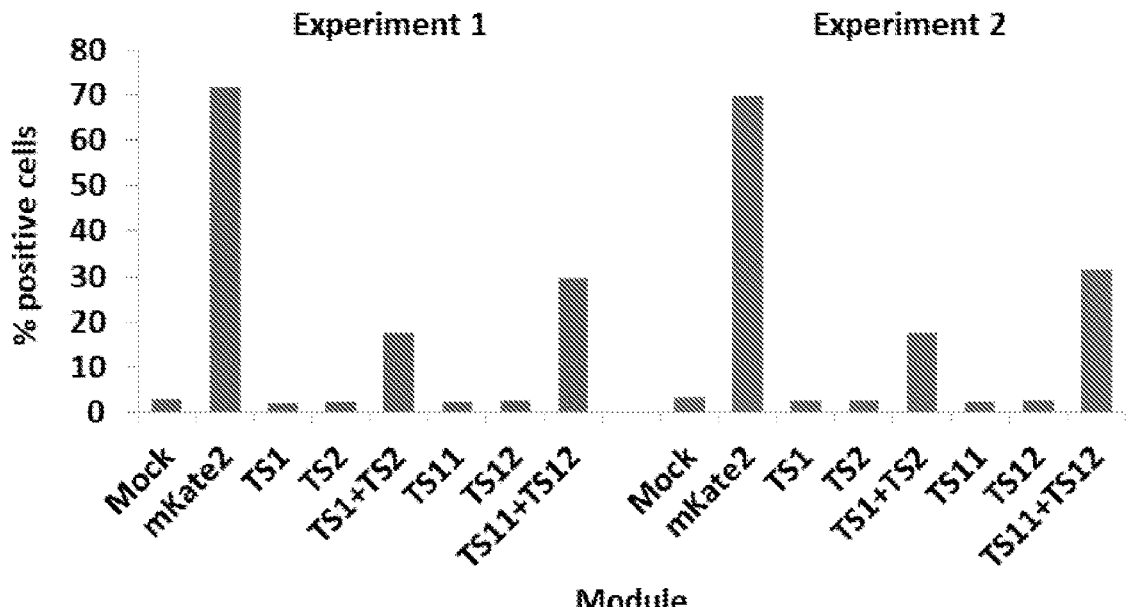
FIG. 4 shows the results of an experiment confirming function of the new 2-module circuits. HEK293T cells ($10^5$) were transfected with either Module TS1, Module TS2, Module TS11 or Module TS12 plasmids alone, each at 1 µg, or both plasmids of each pair together (TS1+TS2 or TS11+TS12) using the FuGENE HD reagent. Irrelevant DNA was used to complement the total amount of DNA to 2 µg in each single transfection. Irrelevant DNA (Mock) was used as a negative control and the mKate2-coding plasmid pLN74 was used to assess transfection yield. The results of two independent experiments are shown as % of mKate2-positive cells as determined by flow cytometry analysis for mKate2 fluorescence according to respective dot plots. Transfected cells were prepared and analyzed by FACS (Attune NxT, Thermo Fisher Scientific) 48 hours post-transfection.

We then continued and assessed the function of our two new circuits. Our design guarantees no expression of the full GOI (in our case the mKate2 fluorophore) upon introduction of each of the two modules alone. The only scenario, which allows expression of the GOI, is the successful TS between the transcripts of the two modules. Accordingly, we have transiently transfected HEK293T cells with either Module 1 or Module 2 plasmids of the two circuits alone, or with a 1:1 mixture of the two, using irrelevant DNA to keep the final amount of DNA in all transfections constant. The mKate2-encoding plasmid pLN74 served for evaluation of transfection efficacy. Results of two independent experiments performed along the same scheme are shown in FIG. 4.

Indeed, as expected, absolutely no mKate2 fluorescence could be detected when cells were transfected with each module separately; yet, a clear signal was evident following co-transfection of the cells with the two modules.
Conclusions.

These experiments clearly demonstrate a proof of concept of our approach:

In both circuits, transfection of each module alone gave rise to zero fluorescence (as expected, since it simply CANNOT result in a closed circuit under any such circumstances), so that our TS-based concept provides a solution to the safety challenge.

Co-transfection of the two modules closed the circuit, yielding clear mKate2 fluorescence.

The second circuit, which included several components that had been designed to improve TS (based on (8)), indeed exhibited greater efficacy than the first circuit which only directed 'basic' TS.

Example 2. Improving TS Efficiency by Calibration of Splicing Site or Binding Domain The logic AND-gate used in Example 1 was used in the following experiments aimed at improving trans-splicing efficiency. SSX1p—was cloned to the first construct which includes the donor site. H2A1p—was cloned to the second construct which includes the 3' acceptor site. All the constructs include a binding domain (BD), a half sequence of a reporter gene (mKAte2)—first half and second half in accordance to first construct and second construct, and an intron sequence—miRV3 (50 bp).

In order to enhance trans-splicing in our AND-gate we have made modifications to the 3' acceptor site or to the BD site of the original constructs described in Example 1 (TS11 and TS12 are referred to here as pKR3 and pKR4a, respectively, and were tested re-evaluated in Sample 1). HEK293T cells were transfected with various combinations of our designs.

Samples 2-4 test various 3' acceptor site sequences; and Samples 6-19 test various binding domain sequences and configurations (see Tables 1 and 2).

TABLE 1

| Sample # (Construct 1/ Construct 2) | BD of Construct-1 (SEQ ID NO.) | BD of Construct-2 (SEQ ID NO.) | 3' Acceptor site (SEQ ID NO.) |
|---|---|---|---|
| 1 (pKR3/pKR4a) | AFP SEQ ID NO: 1 | AFP SEQ ID NO: 2 | AFP SEQ ID NO: 17 |
| 2 (pKR3/pKR5) | AFP SEQ ID NO: 1 | AFP SEQ ID NO: 2 | Consensus SEQ ID NO: 18 |
| 3 (pKR3/PKR6) | AFP SEQ ID NO: 1 | AFP SEQ ID NO: 2 | HSV-I SEQ ID NO: 19 |
| 4 (pKR3/PKR7) | AFP SEQ ID NO: 1 | AFP SEQ ID NO: 2 | pHA16 SEQ ID NO: 20 |
| 5 (pKR3/PKR11) | AFP SEQ ID NO: 1 | AFP SEQ ID NO: 3 | AFP SEQ ID NO: 17 |
| 6 (pKR10/PKR9) | AFP SEQ ID NO: 4 | AFP SEQ ID NO: 5 | AFP SEQ ID NO: 17 |
| 7 (pKR10/PKR4a) | AFP SEQ ID NO: 4 | AFP SEQ ID NO: 2 | AFP SEQ ID NO: 17 |
| 8 (pKR3/PKR9) | AFP SEQ ID NO: 1 | AFP SEQ ID NO: 5 | AFP SEQ ID NO: 17 |
| 9 (pKR13/PKR12) | AFP SEQ ID NO: 6 | AFP SEQ ID NO: 7 | AFP SEQ ID NO: 17 |
| 10 (pKR13/PKR4a) | AFP SEQ ID NO: 6 | AFP SEQ ID NO: 2 | AFP SEQ ID NO: 17 |
| 11 (pKR3/PKR12) | AFP SEQ ID NO: 1 | AFP SEQ ID NO: 7 | AFP SEQ ID NO: 17 |
| 12 (pKR13/PKR9) | AFP SEQ ID NO: 6 | AFP SEQ ID NO: 5 | AFP SEQ ID NO: 17 |
| 13 (pKR10/PKR12) | AFP SEQ ID NO: 4 | AFP SEQ ID NO: 7 | AFP SEQ ID NO: 17 |
| 14 (pKR14/PKR4a) | AFP SEQ ID NO: 8 | AFP SEQ ID NO: 2 | AFP SEQ ID NO: 17 |
| 15 (pKR14/PKR11) | AFP SEQ ID NO: 8 | AFP SEQ ID NO: 3 | AFP SEQ ID NO: 17 |
| 16 (pKR15/PKR16) | SEQ ID NO: 9 | SEQ ID NO: 10 | SEQ ID NO: 17 |
| 17 (pKR17/PKR18) | SEQ ID NO: 11 | SEQ ID NO: 12 | AFP SEQ ID NO: 17 |
| 18 (pKR19/PKR20) | SEQ ID NO: 13 | SEQ ID NO: 14 | AFP SEQ ID NO: 17 |
| 19 (pKR21/PKR22) | SEQ ID NO: 15 | SEQ ID NO: 16 | AFP SEQ ID NO: 17 |
| 20 (pKR3/PKR16) | AFP SEQ ID NO: 1 | AFP SEQ ID NO: 10 | AFP SEQ ID NO: 17 |
| 21 (pKR15/PKR4a) | AFP SEQ ID NO: 9 | AFP SEQ ID NO: 2 | AFP SEQ ID NO: 17 |
| 22 (pKR14/PKR5) | AFP SEQ ID NO: 8 | AFP SEQ ID NO: 2 | AFP SEQ ID NO: 17 |
| 23 (pKR14/PKR14) | AFP SEQ ID NO: 8 | AFP SEQ ID NO: 8 | AFP SEQ ID NO: 17 |
| 24 (pKR4a/PKR4a) | AFP SEQ ID NO: 2 | AFP SEQ ID NO: 2 | AFP SEQ ID NO: 17 |

AFP-Binding domain (BD) of Alpha-fetoprotein but sequence is reversed.

Consensus-A 'consensus' acceptor, donor, and branching sequences. (Smith, C. W. J., Porro, E. B., Patton, J. G., and Nadal-Ginard, B. (1989). Scanning from an independently specified branch point defines the 3[prime] splice site of mammalian introns. Nature 342, 243-247); Taggart, A. J., DeSimone, A. M., Shih, J. S., Filloux, M. E., and Fairbrother, W. G. (2012). Largescale mapping of branchpoints in human pre-mRNA transcripts in vivo. Nature structural & molecular biology 19, 719-721.
HSV-Herpes Simplex Virus acceptor, donor, and branching sequences.
pHA16-mutated 'consensus' sequence developed in the Nissim lab.

TABLE 2

| Complement configuration between BD of Construct-1 and BD of Construct-2 | |
|---|---|
| S# | BD sequence of Construct-1 / BD sequence of Construct-2 |
| 1. | 5TGGAGAGATTTGGATTTTTTTAAA AGAAGAGATTTGGAGAAAGGATCAA 3ACCTCTCTAAACCTAAATTAAATTT TCTTCTCTAAACCTCTTT<u>CC</u>TAGTT |

| 23 | 24 |
|---|---|
| TABLE 2-continued | TABLE 2-continued |

TABLE 2-continued

Complement configuration between BD of
Construct-1 and BD of Construct-2

| S# | BD sequence of Construct-1<br>BD sequence of Construct-2 |
|---|---|
| 2. | 5TGGAGAGATTTGGATTTTTTTTAAA<br>AGAAGAGATTTGGAGAAAGGATCAA<br>3ACCTCTCTAAACCTAAATTAAATTT<br>TCTTCTCTAAACCTCTTT<u>CC</u>TAGTT |
| 3. | 5TGGAGAGATTTGGATTTTTTTTAAA<br>AGAAGAGATTTGGAGAAAGGATCAA<br>3ACCTCTCTAAACCTAAATTAAATTT<br>TCTTCTCTAAACCTCTTT<u>CC</u>TAGTT |
| 4. | 5TGGAGAGATTTGGATTTTTTTTAAA<br>AGAAGAGATTTGGAGAAAGGATCAA<br>3ACCTCTCTAAACCTAAATTAAATTT<br>TCTTCTCTAAACCTCTTT<u>CC</u>TAGTT |
| 5. | 5TGGAGAGATTTGGATTTTTTTTAAA<br>AGAAGAGATTTGGAGAAAGGATCAA<br>3ACCTCTCTAAACCTAAAAAAAATTT<br>TCTTCTCTAAACCTCTTTCCTAGTT |
| 6. | 5 TTAAAAGAAGAGATTTGGAGAAAG<br>GATCAA<br>3AATTTTCTTCTCTAAACCTCTTTCC<br>TAGTT |
| 7. | 5 TTAAAAGAAGAGATTTGGAGAAAG<br>GATCAA<br>3ACCTCTCTAAACCTAAATTAAATTT<br>TCTTCTCTAAACCTCTTT<u>CC</u>TAGTT |
| 8. | 5TGGAGAGATTTGGATTTTTTTTAAA<br>AGAAGAGATTTGGAGAAAGGATCAA<br>3AATTTTCTTCTCTAAACCTCTTTCC<br>TAGTT |
| 9. | 5TGGAGAGATTTGGATTTTTTTTAAA<br>AGAAG<br>3ACCTCTCTAAACCTAAAAAAAATTT<br>TCTTC |
| 10. | 5TGGAGAGATTTGGATTTTTTTTAAA<br>AGAAG<br>3ACCTCTCTAAACCTAAATTAAATTT<br>TCTTCTCTAAACCTCTTT<u>CC</u>TAGTT |
| 11. | 5TGGAGAGATTTGGATTTTTTTTAAA<br>AGAAGAGATTTGGAGAAAGGATCAA<br>3ACCTCTCTAAACCTAAAAAAAATTT<br>TCTTC |
| 12. | 5TGGAGAGATTTGGATTTTTTTTAAA<br>AGAAG<br>3AATTTTCTTCTCTAAACCTCTTTCC<br>TAGTT |
| 13. | 5 TTAAAAGAAGAGATTTGGAGAAAGG<br>ATCAA<br>3 ACCTCTCTAAACCTAAAAAAAATT<br>TTCTTC |
| 14. | TGGAGAGATTTGGATTTTTTTTAAAAG<br>AAGAGATTTGGAGAAAGGATCAATCGCA<br>TGGAGAGATTTGGATTTTTTTTAAAAGA<br>AGAGATTTGGAGAAAGGATCAAACCTCT<br>CTAAACCTAAATTAAATTTTCTTCTCTA<br>AACCTCTTTCC<u>TAGTT</u><br>OR<br>ACCTCTCTAAACCTAAATTAAATTTTCT<br>TCTCTAAACCTCTTTCC<u>TAGTT</u> |
| 15. | TGGAGAGATTTGGATTTTTTTTAAAAGAA<br>GAGATTTGGAGAAAGGATCAATCGCATGG<br>AGAGATTTGGATTTTTTTTAAAAGAAGAG<br>ATTTGGAGAAAGGATCAAACCTCTCTAAA |

Complement configuration between BD of
Construct-1 and BD of Construct-2

| S# | BD sequence of Construct-1<br>BD sequence of Construct-2 |
|---|---|
| | CCTAAAAAAAATTTTCTTCTCTAAACCTC<br>TTTCCTAGTT<br>OR<br>AACCTCTCTAAACCTAAAAAAAATTTTCTT<br>CTCTAAACCTCTTTCCTAGTT |
| 16. | 5 CAAGAAGGTACTGGCTGCTATTATACG<br>AAGTGCCGTTGCAGGATCTCCTG<br>3GTTCTTCCATGACCGACGATAATATGCT<br>TCACGGCAACGTCCTAGAGGAC |
| 17. | 5 CATTATATCATGAAACATCACTTCTTA<br>TAATAGCATTCAGTACCTTCTTG<br>3GTAATATAGTACTTTGTAGTGAAGAATA<br>TTATCGTAAGTCATGGAAGAAC |
| 18. | 5 ATCAGGATGATCTGGACGAAGAGCATC<br>AGG<br>3TAGTCCTACTAGACCTGCTTCTCGTAGT<br>CC |
| 19. | 5 TATATGAACATTCTACCACAAATCGAA<br>ACA<br>3ATATACTTGTAAGATGGTGTTTAGCTTT<br>GT |
| 20. | 5TGGAGAGATTTGGATTTTTTTTAAAAGA<br>AGAGATTTGGAGAAAGGATCAA<br>3GTTCTTCCATGACCGACGATAATATGCT<br>TCACGGCAACGTCCTAGAGGAC |
| 21. | 5 CAAGAAGGTACTGGCTGCTATTATACG<br>AAGTGCCGTTGCAGGATCTCCTG<br>3ACCTCTCTAAACCTAAATTAAATTTTCT<br>TCTCTAAACCTCTTTCC<u>TAGTT</u> |
| 22. | TGGAGAGATTTGGATTTTTTTTAAAAGAA<br>GAGATTTGGAGAAAGGATCAATCGCATGG<br>AGAGATTTGGATTTTTTTTAAAAGAAGAG<br>ATTTGGAGAAAGGATCAAACCTCTCTAAA<br>CCTAAATTAAATTTTCTTCTCTAAACCTC<br>TTTCC<u>TAGTT</u><br>OR<br>ACCTCTCTAAACCTAAATTAAATTTTC<br>TTCTCTAAACCTCTTTC<u></u><br>CTAGTT |
| 23. | TGGAGAGATTTGGATTTTTTTTAAAAGAA<br>GAGATTTGGAGAAAGGATCAATCGCATGG<br>AGAGATTTGGATTTTTTTTAAAAGAAGAG<br>ATTTGGAGAAAGGATCAA<br>TGGAGAGATTTGGATTTTTTTTAAAAGAA<br>GAGATTTGGAGAAAGGATCAATCGCATGG<br>AGAGATTTGGATTTTTTTTAAAAGAAGAG<br>ATTTGGAGAAAGGATCAA |
| 24. | TTGATCCTTTCTCCAAATCTCTTCTTTTA<br>AATTAAATCCAAATCTCTCCA<br>ACCTCTCTAAACCTAAATTAAATTTTCTT<br>CTCTAAACCTCTTTCCTAGTT |

Figure 5:
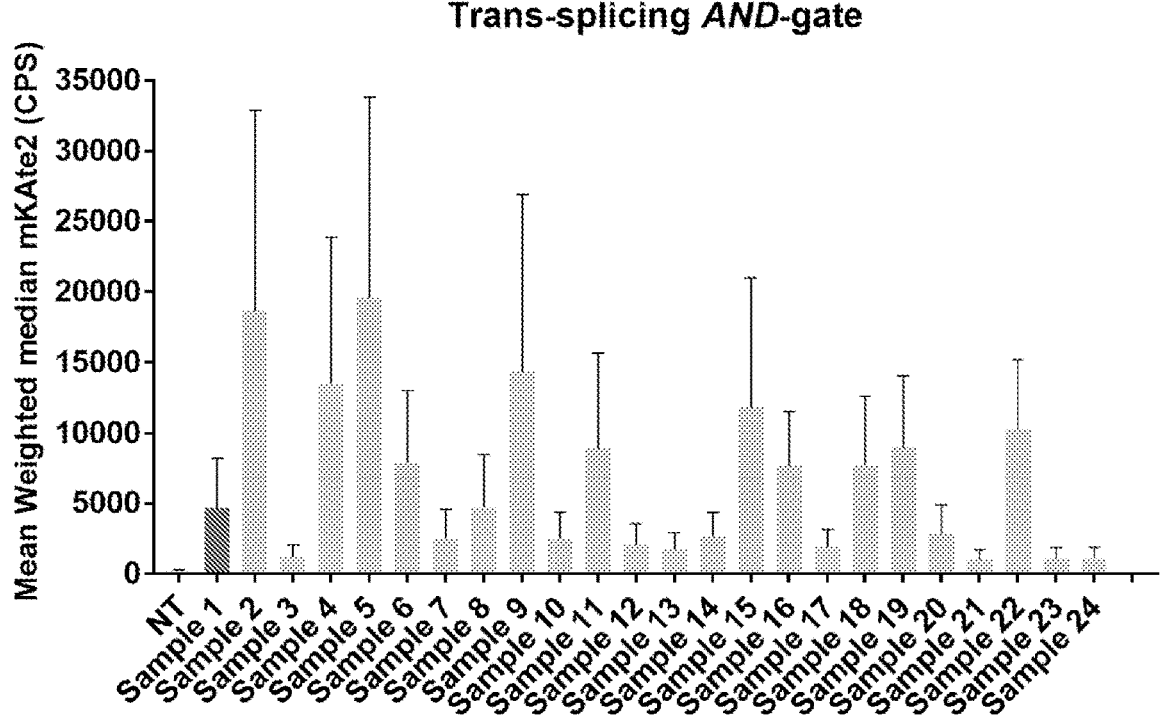
FIG. 5 shows analysis of trans-splicing AND-gate efficiency. The new structures' activities of trans-splicing AND-gate with different 3' Acceptor sites (sample 2-4) or Binding Domain sequences (sample 5-23) relative to the parental construct—sample 1 (second from left). Negative control.

Nucleotides in bold and underline are mismatched. For the
specific sequences see Table 1.
S#, Sample number Results We tested the original AFP binding and splicing
sequences, as well as other designs. As can be seen in FIG.
5, some of our designs worked better than the original AFP
binding and splicing sequences. For example, while the
original AFP design works relatively well (Sample 1 and
Example 1), switching the splicing acceptor sequence from
AFP to consensus resulted in about 4-fold increase of the
output levels (Sample 2), changing the mismatches in the original design into matching codons also resulted in about 4-fold increase of the output levels (Sample 5), and shortening the original BD to only 30 bp resulted in about 3-fold increase of the output levels (Sample 9). Thus, we have designed constructs that are superior to the original AFP binding and splicing sequences.

Materials & Methods.

| Material | Cat. No. | Manufacturer |
|---|---|---|
| DMEM, High Glucose, 500 ml | 41965-039 | Gibco |
| Fetal Bovine Serum, 500 ml | 04-007-1A | Biological Industries |
| Opti-MEM ® Reduced Serum Medium | 31985-047 | Gibco |
| QIAGEN Plasmid Plus Midi Kit (100) | 20-12945 | Qiagen |
| FuGENE ® HD Transfection Reagent | E2311 | Promega |
| Dulbecco's Phosphate Buffered Saline (DPBS) | 02-023-1A | Biological Industries |
| Trypsin EDTA Solution A (0.25%), EDTA (0.02%)*With Phenol Red | 03-050-1B | Biological Industries |
| L-Glutamine Solution; 29.2 mg/ml in Saline (200 mM) | 03-020-1B | Biological Industries |
| Sodium Pyruvate Solution, 11.0 mg/ml (100 mM) | 03-042-1B | Biological Industries |
| Penicillin-Streptomycin Solution, *10,000 units/ml Penicillin G Sodium Salt, *10 mg/ml Streptomycin Sulfate | 03-031-1B | Biological Industries |
| MEM EAGLE*Non-essential amino acids solution*Concentrate X 100 | 01-340-1B | Biological Industries |
| HEK293T | CRL-1573 | ATCC |

Experimental Model and Subject Details

Cell Culture and Cell Lines

HEK293T, cells were obtained from the American Type Culture Collection, Rockville, Md. (HEK293T, Catalog #CRL-1573). HEK293T cells were cultured in DMEM (Gibco) supplemented with 10% fetal bovine serum (FBS; Biological Industries; Catalog #04-007-1A), 1% Non-Essential Amino Acids (MEM/NEAA; Biological Industries; Catalog #01-340-1B), and 1% Pen/Strep (Biological Industries #03-031-1B) at 37° C. with 5% CO2. All cell lines were banked directly after being purchased from vendors and used at low passage numbers.

Plasmid Construction

The various constructs were built using conventional restriction enzyme cloning and Gibson assembly. All the DNAs were purified by QIAGEN Plasmid Plus Midi Kit (Plasmid Plus Midi Kit; QIAGEN; Catalog #20-12945)

Transfection

In this study we tested different combinations of two plasmids: construct1 variants expressed the first half-mKate2 RNA transcript and construct 2 variants expressed the second half mKate2 transcript. mKate2 enables us to assess Trans splicing expression. In brief, 8 µL of FuGENE HD transfection reagent (Promega, Madison, Wis.; Catalog #E2311) mixed with 100 µL of OptiMEM medium (Life Technologies Catalog #31985) was added to the mixture of two plasmids (1 µg each). During 20 minutes incubation of FuGENE HD/DNA complexes at room temperature, HEK293T suspension cells were prepared and diluted to $1.2 \times 10^6$ cells/mL in culture medium. 0.5 mL of diluted cells ($0.6 \times 10^6$ cells) were added to each FuGENE HD/DNA complex tube, mixed well, and transferred to a designated well in 6-well plate containing 2 mL cell culture medium, followed by incubation at 37° C. with 5% CO2. Transfected cells were prepared for FACS analysis at 48-hour post-transfection.

Example 3. Multi-Output AND Gate for Combinatorial Immunomodulation

To facilitate the expression of combinatorial immuno-modulators (an immunogenic cell-surface antigen), a chemokine, a cytokine, and an immune checkpoint inhibitor from our circuit, we replace mKate2 in modules 1 and 2 with a synthetic transcription factor GAD that binds to its cognate synthetic promoter and activates the expression of downstream genes according to Nissim et al. (supra). This GAD was previously made by fusing the yeast GAL4 DNA-binding domain to the viral VP16 transcriptional activation domain and can be cloned e.g. from a mammalian two-hybrid system construct marketed by Promega (Catalog number E2440). Module 1, encoding one incomplete fragment of GAD, may be regulated by a tumor-specific promoter 1, and Module 2, encoding the complementing incomplete fragment of GAD, may be regulated by a tumor-specific promoter 2. Trans-splicing will provide an mRNA encoding for the complete GAD transcription factor. We thus expect specific expression of the immunomodulators when both input promoters are mutually active in the target cell.

Example 4. Treatment of Cancer

Based on Nissim et al (supra) the synthetic expression of the present invention is organized into a pertinent number of lentiviruses. Mice with i.p. disseminated OV8 tumors are injected i.p. with either a control lentivirus mix that contains module 1, module 2, and a negative control output or a therapeutic virus mix that contains module 1, module 2, and the SCIP outputs. Human T cells are also periodically injected i.p. Under these settings, we expect significantly reduced tumor burden and enhanced survival in mice treated with the SCIP circuit versus the control unit.

REFERENCES

1. Dong, Z., and J. E. Nör. 2009. Transcriptional targeting of tumor endothelial cells for gene therapy. *Adv. Drug Deliv. Rev.* 61: 542-553.
2. Nissim, L., M.-R. Wu, E. Pery, A. Binder-Nissim, H. I. Suzuki, D. Stupp, C. Wehrspaun, Y. Tabach, P. A. Sharp, and T. K. Lu. 2017. Synthetic RNA-Based Immunomodulatory Gene Circuits for Cancer Immunotherapy. *Cell* 171: 1138-1150.e15.
3. Yang, Y., and C. E. Walsh. 2005. Spliceosome-Mediated RNA Trans-splicing. *Mol. Ther.* 12: 1006-1012.
4. Puttaraju, M., S. F. Jamison, S. G. Mansfield, M. A. Garcia-Blanco, and L. G. Mitchell. 1999. Spliceosome-mediated RNA trans-splicing as a tool for gene therapy. *Nat. Biotechnol.* 17: 246-252.
5. Puttaraju, M., J. DiPasquale, C. C. Baker, L. G. Mitchell, and M. A. Garcia-Blanco. 2001. Messenger RNA repair and restoration of protein function by spliceosome-mediated RNA trans-splicing. *Mol. Ther.* 4: 105-14.
6. Suñé-Pou, M., S. Prieto-Sánchez, S. Boyero-Corral, C. Moreno-Castro, Y. El Yousfi, J. Suñé-Negre, C. Hernández-Munain, and C. Suñé. 2017. Targeting Splicing in the Treatment of Human Disease. *Genes (Basel).* 8: 87.
7. Schlesinger, J., D. Arama, H. Noy, M. Dagash, P. Belinky, and G. Gross. 2003. In-cell generation of antibody single-chain Fv transcripts by targeted RNA trans-splicing. *J Immunol Methods* 282: 175-186.

8. Poddar, S., P. S. Loh, Z. H. Ooi, F. Osman, J. Eul, and V. Patzel. 2018. RNA Structure Design Improves Activity and Specificity of trans-Splicing-Triggered Cell Death in a Suicide Gene Therapy Approach. *Mol. Ther.—Nucleic Acids* 11: 41-56.

9. Ohana, P., O. Bibi, I. Matouk, C. Levy, T. Birman, I. Ariel, T. Schneider, S. Ayesh, H. Giladi, M. Laster, N. de Groot, and A. Hochberg. 2002. Use of H19 regulatory sequences for targeted gene therapy in cancer. *Int. J. Cancer* 98: 645-650.

10. Fellig, Y., I. Ariel, P. Ohana, P. Schachter, I. Sinelnikov, T. Birman, S. Ayesh, T. Schneider, N. de Groot, A. Czerniak, and A. Hochberg. 2005. H19 expression in hepatic metastases from a range of human carcinomas. *J. Clin. Pathol.* 58: 1064-8.

11. Ariel, I., M. Sughayer, Y. Fellig, G. Pizov, S. Ayesh, D. Podeh, B. A. Libdeh, C. Levy, T. Birman, M. L. Tykocinski, N. de Groot, and A. Hochberg. 2000. The imprinted H19 gene is a marker of early recurrence in human bladder carcinoma. *Mol. Pathol.* 53: 320-3.

12. Pleshkan, V. V, I. V Alekseenko, M. V Zinovyeva, T. V Vinogradova, and E. D. Sverdlov. 2011. Promoters with cancer cell-specific activity for melanoma gene therapy. *Acta Naturae* 3: 13-21.

13. Robson, T., and D. G. Hirst. 2003. Transcriptional Targeting in Cancer Gene Therapy. *J. Biomed. Biotechnol.* 2003: 110-137.

14. Morgan, D. O. 1997. Cyclin-dependent kinases: engines, clocks, and microprocessors. *Annu. Rev. Cell Dev. Biol.* 13: 261-91.

15. Müller, H., A. P. Bracken, R. Vernell, M. C. Moroni, F. Christians, E. Grassilli, E. Prosperini, E. Vigo, J. D. Oliner, and K. Helin. 2001. E2Fs regulate the expression of genes involved in differentiation, development, proliferation, and apoptosis. *Genes Dev.* 15: 267-85.

16. Whitfield, M. L., G. Sherlock, A. J. Saldanha, J. I. Murray, C. A. Ball, K. E. Alexander, J. C. Matese, C. M. Perou, M. M. Hurt, P. O. Brown, and D. Botstein. 2002. Identification of Genes Periodically Expressed in the Human Cell Cycle and Their Expression in Tumors. *Mol. Biol. Cell* 13: 1977-2000.

17. Tsantoulis, P. K., and V. G. Gorgoulis. 2005. Involvement of E2F transcription factor family in cancer. *Eur. J. Cancer* 41: 2403-14.

18. PJ, R. 2016. What Have We Learned About Synthetic Promoter Construction?*Methods Mol. Biol.* 1482.

19. Matuskova, M., and E. Durinikov. 2016. Retroviral Vectors in Gene Therapy. In *Advances in Molecular Retrovirology* InTech.

20. Izsvák, Z., and Z. Ivics. 2004. Sleeping Beauty Transposition: Biology and Applications for Molecular Therapy. *Mol. Ther.* 9: 147-156.

The invention claimed is:

1. A synthetic nucleic acid expression system for production of a transcript of interest in a cell-state, the system comprising, a) a first nucleic acid sequence comprising a first promoter operably linked to a nucleic acid sequence encoding a first trans-spliceable pre-mRNA sequence comprising at least one exon encoding a 5' fragment of said transcript of interest and a first RNA sequence required for spliceosome-dependent trans-splicing, wherein said first RNA sequence required for spliceosome-dependent trans-splicing comprises a donor site for splicing and a first hybridization sequence; and b) a second nucleic acid sequence comprising a second promoter operably linked to a nucleic acid sequence encoding a second trans-spliceable pre-mRNA sequence comprising at least one exon encoding a 3' fragment of said transcript of interest and a second RNA sequence required for spliceosome-dependent trans-splicing wherein said first RNA sequence required for spliceosome-dependent trans-splicing comprises an acceptor site for splicing and a second hybridization sequence;

wherein said first promoter and said second promoter are different and each one is active in said cell-state, wherein said first hybridization sequence is complementary to said second hybridization sequence, and wherein said first and said second hybridization sequences lack 100% base complementarity with each transcript of the innate transcriptome of said cell-state, and each one of said at least one exons encodes an incomplete transcript of interest, and a messenger RNA comprising said at least one exon encoding a 5' fragment of said transcript of interest joined to said at least one exon encoding a 3' fragment of said transcript of interest encodes a complete transcript of interest.

2. The synthetic expression system of claim 1, wherein said first nucleic acid sequence and said second nucleic acid sequence are present on the same nucleic acid molecule.

3. The synthetic expression system of claim 1, wherein the first and second nucleic acid sequences are present on separate nucleic acid molecules.

4. The synthetic expression system of claim 1, wherein said cell-state is selected from the group consisting of a cell type, tissue type, cell-cycle phase, metabolic state, pathological state, differentiation state, epigenetic state, and activation state.

5. The synthetic expression system of claim 1, wherein each one of said first and said second promoter independently is selected from the group consisting of a cell-type-specific promoter, a tissue-specific promoter, a disease-specific promoter and a cell-cycle responsive promoter.

6. The synthetic expression system of claim 5, wherein each one of said first and said second promoter independently is a disease-specific promoter, optionally a tumor-specific promoter.

7. The synthetic expression system of claim 1, wherein said incomplete transcript of interest is a non-functional transcript or encodes a non-functional protein.

8. The synthetic expression system of claim 1, wherein said transcript of interest encodes a transcript product selected from the group consisting of a transcription factor, a synthetic transcription factor; a native transcription factor; a cell surface protein, a chemokine, a cytokine, a checkpoint inhibitor, an enzyme; a growth factor; a reporter gene; a short hairpin RNA (shRNA); and a micro RNA (miRNA).

9. A eukaryotic cell comprising the synthetic expression system of claim 1.

10. A method for treating a patient or cells obtained from said patient afflicted with a disease associated with or caused by a cell-state, the method comprising contacting cells of said patient with at least one vector comprising the first nucleic acid sequence (a) and the second nucleic acid sequence (b) of the synthetic expression system of claim 1, wherein each one of said first and second promoter independently is specifically regulated by said cell-state, and said transcript of interest encodes a transcript product facilitating treatment of said disease, thereby expressing said transcript of interest solely in said cell-state and treating said disease.

11. The method of claim 10, comprising contacting said cells with two different vectors, wherein one of said two vectors comprises the first nucleic acid sequence (a) but not the second nucleic acid sequence (b); and the other of said two vectors comprises the second nucleic acid sequence (b) but not the first nucleic acid sequence (a).

12. The method of claim 10, wherein said cell state is selected from the group consisting of a cell type, tissue type, cell-cycle phase, metabolic state, pathological state, differentiation state, epigenetic state, and activation state.

13. The method of claim 12, wherein each one of said first and said second promoter independently is specifically induced or activated by said cell-state.

14. The method of claim 12, wherein each one of said first and said second promoter independently is selected from a cell-type-specific promoter, a tissue-specific promoter, a disease-specific promoter, a differentiation state specific promoter, an epigenetic state specific promoter, an activation state specific promoter and a cell-cycle responsive promoter.

15. The method of claim 14, wherein said patient is a human patient.

16. The method of claim 14, wherein said disease is cancer and each one of said first and said second promoter is a tumor-specific promoter.

17. The method of claim 10, wherein said transcript product facilitating treatment of said disease is a transcription factor, e.g. synthetic transcription factor; a chemokine; a cytokine; a checkpoint inhibitor; an auxotrophic marker; an enzyme; a growth factor; a short hairpin RNA (shRNA), or a micro RNA (miRNA).

18. The synthetic expression system of claim 1, wherein said first hybridization sequence and said second hybridization sequence are each 10-40 nucleotides long.

19. The synthetic expression system of claim 1, wherein said first hybridization sequence and said second hybridization sequence are less than 100% complementary to each other and comprise at least one mismatched nucleotide.

20. A synthetic nucleic acid expression system for production of a transcript of interest in a cell, the system comprising, a) a first nucleic acid sequence comprising a first promoter operably linked to a nucleic acid sequence encoding a first trans-spliceable pre-mRNA sequence comprising at least one exon encoding a 5' fragment of said transcript of interest, a donor site for splicing and a first hybridization sequence; and b) a second nucleic acid sequence comprising a second promoter operably linked to a nucleic acid sequence encoding a second trans-spliceable pre-mRNA sequence comprising at least one exon encoding a 3' fragment of said transcript of interest, an acceptor site for splicing and a second hybridization sequence;

wherein said first promoter and said second promoter are different, wherein said first hybridization sequence is complementary to said second hybridization sequence and comprises at least one mismatch with said second hybridization sequence, and wherein said first and said second hybridization sequences lack base complementarity with each transcript of the innate transcriptome of said cell, and each one of said at least one exons encodes an incomplete transcript of interest, and a messenger RNA comprising said at least one exon encoding a 5' fragment of said transcript of interest joined to said at least one exon encoding a 3' fragment of said transcript of interest encodes a complete transcript of interest.

* * * * *